(12) United States Patent
Laulicht et al.

(10) Patent No.: US 9,999,690 B2
(45) Date of Patent: Jun. 19, 2018

(54) LABELED COMPOUNDS AND METHODS OF IMAGING, DIAGNOSING CARTILAGE DISORDERS AND DISEASES, AND MONITORING CARTILAGE HEALTH USING LABELED AND UNLABELED COMPOUNDS

(71) Applicant: Perosphere Inc., Danbury, CT (US)

(72) Inventors: Bryan E. Laulicht, Danbury, CT (US); Sasha H. Bakhru, Ridgefield, CT (US); James Costin, Lower Gwynedd, PA (US); Solomon S. Steiner, Mount Kisco, NY (US)

(73) Assignee: PEROSPHERE PHARMACEUTICALS INC., Danbury, CT (US)

( * ) Notice: Subject to any disclaimer, the term of this patent is extended or adjusted under 35 U.S.C. 154(b) by 447 days.

(21) Appl. No.: 14/534,474

(22) Filed: Nov. 6, 2014

(65) Prior Publication Data

US 2015/0133769 A1    May 14, 2015

Related U.S. Application Data

(60) Provisional application No. 61/901,646, filed on Nov. 8, 2013, provisional application No. 61/930,705, filed on Jan. 23, 2014.

(51) Int. Cl.

| A61K 49/10 | (2006.01) |
|---|---|
| A61K 51/04 | (2006.01) |
| A61B 6/00 | (2006.01) |
| G01R 33/56 | (2006.01) |
| A61B 5/00 | (2006.01) |
| A61B 5/055 | (2006.01) |

(52) U.S. Cl.
CPC .......... *A61K 49/10* (2013.01); *A61K 51/0459* (2013.01); *A61B 5/055* (2013.01); *A61B 5/4514* (2013.01); *A61B 6/481* (2013.01); *A61B 6/505* (2013.01); *A61B 6/508* (2013.01); *G01R 33/5601* (2013.01)

(58) Field of Classification Search
CPC ................................. A61K 49/00; A61K 51/04
See application file for complete search history.

(56) References Cited

U.S. PATENT DOCUMENTS

| 4,560,548 A | 12/1985 | Simon et al. | |
|---|---|---|---|
| 6,248,356 B1 | 6/2001 | Tracey et al. | |
| 7,517,990 B2 * | 4/2009 | Ito | C07B 59/002 546/184 |
| 9,522,892 B2 | 12/2016 | Steiner et al. | |
| 9,877,961 B2 | 1/2018 | Steiner et al. | |
| 2006/0148734 A1 * | 7/2006 | Camilleri | C07C 237/22 514/44 R |
| 2010/0240894 A1 | 9/2010 | Ernst et al. | |

FOREIGN PATENT DOCUMENTS

| WO | WO2006051489 | * 5/2006 |
|---|---|---|
| WO | 2011/146759 A2 | 11/2011 |
| WO | 2013/082210 A1 | 6/2013 |

OTHER PUBLICATIONS

Takayoshi Irie et at, "Design, Synthesis, and Preliminary Ex Vivo and in Vivo Evaluation of Cationic Magnetic Resonance Contrast Agent for Rabbit Articular Cartilage Imaging," 4(11) Med. Chem. Comm. 1508-1512 (Sep. 2013).
International Search Report in International Application No. PCT/US2014/064257 (Mar. 2015).
International Preliminary Report on Patentability with Written Opinion in International Application No. PCT/US2014/064257 (May 2016).
Deva D. Chan et al., "Probing articular cartilage damage and disease by Quantitative Magnetic Resonance Imaging," 10 J. R. Soc. Interface 1-11 (Nov. 2012).
Todd B. Parrish et al., "Impact of Signal-to-Noise on Functional MRI," 44(6) Magn. Reson. Med. 925-932 (Dec. 2000).
Maureen N. Hood et al., "Chemical Shift: The Artifact and Clinical Tool Revisited," 19(2) RSNA Radiographics 357-371 (Mar. 1999).
Yan Yang et al., "1H Chemical Shift Magnetic Resonance Imaging Probes with High Sensitivity for Multiplex Imaging," 7(2) Contrast Media Mol. Image 276-279 (Mar.-Apr. 2012).
The National Institute of Mental Health: "Proton Chemical Shift Imaging of Human Brain," pp. 1-2 (downloaded Oct. 2017) (https://www.nimh.nih.gov/labs-at-nimh/research-areas/research-support-services/mrs/pcsih.shtml).
Libby Brateman, "Chemical Shift Imaging: A Review," 146(5) Am. J. Roentgenol. 971-980 (May 1986).
Pieter Zanen et al., "The Optimal Particle Size for Parasympathicolytic Aerosols in Mild Asthmatics," 114(1) Int. J. Pharm. 111-115 (Jan. 1995).
Terry Stanton, "New Techniques Improve Cartilage Imaging; dGEMRIC Leads Pack of New Biochemical Methods," AAOS Now, Apr. 2011 (http://www.aaos.org/news/aaosnow/apr11/clinical7.asp).
Akwete Adjei et al., "Pulmonary Delivery of Peptide Drugs: Effect of Particle Size on Bioavailability of Leuprolide Acetate in Healthy Male Volunteers," 7(6) Pharm. Res. 565-569 (Jun. 1990).
T.W. Redpath, "Signal-to-noise Ratio in MRI," 71 Br. J. Radiology 704-707 (Jul. 1998).

(Continued)

*Primary Examiner* — Michael G Hartley
*Assistant Examiner* — Jagadishwar R Samala
(74) *Attorney, Agent, or Firm* — Fitzpatrick, Cella, Harper & Scinto

(57) ABSTRACT

Novel labeled compounds and metabolites thereof are disclosed, as well as pharmaceutical compositions including the compounds, and methods of using the labeled and unlabeled compounds, and specifically, 2-Amino-5-guanidino-pentanoic acid (3-{4-[3-(2-amino-5-guanidino-pentanoylamino)-propyl]-piperazin-1-yl}-propyl)-amide and metabolites thereof, for imaging, detecting and assessing disorders and diseases, such as arthritis and, more specifically, osteoarthritis by tracking proteoglycan and glycosaminoglycan content of cartilage. Also, pharmaceutical compositions comprising labeled and/or unlabeled 1,4-Bis (3-aminopropyl)piperazine are disclosed and methods of using the same.

38 Claims, 7 Drawing Sheets

(56) References Cited

OTHER PUBLICATIONS

Marielouise Henrich et al., "A New Family of Delocalized Lipophilic Cations," 44(31) Tet. Lett. 5795-5798 (Jul. 2003).
Hale Ersoy et al., "Contrast Agents for Cardiovascular MRI," Cardiovascular Magnetic Resonance Imaging, R. Kwong, ed., Humana Press Inc., Chapter 10, pp. 237-254 (2008).
Rachel K. Surowiec et al., "Quantitative MRI in the Evaluation of Articular Cartilage Health: Reproducibility and Variability with a Focus on T2 Mapping," 22(6) Knee Surg. Sports Traumatol. Arthrosc. 1385-1395 (Oct. 2013).
Igor Gonda, "Aerosols for Delivery of Therapeutic and Diagnostic Agents to the Respiratory Tract," 6(4) Critical Reviews in Therapeutic Drug Carrier Systems 273-313 (1990).

\* cited by examiner

LABELED COMPOUNDS AND METHODS OF IMAGING, DIAGNOSING CARTILAGE DISORDERS AND DISEASES, AND MONITORING CARTILAGE HEALTH USING LABELED AND UNLABELED COMPOUNDS

The application claims the benefit of priority from U.S. Provisional Application No. 61/901,646, filed Nov. 8, 2013, and U.S. Provisional Application No. 61/930,705, filed on Jan. 23, 2014, the contents of both of which are incorporated by reference herein in their entireties.

FIELD OF THE INVENTION

The present invention discloses novel labeled compounds, pharmaceutical compositions containing the labeled compounds, and methods of imaging using labeled and unlabeled compounds and metabolites as imaging agents in radiography and magnetic resonance imaging, and particularly in chemical shift imaging. Also disclosed are methods of monitoring cartilage health, and diagnosing a cartilage disorder or cartilage disease, including, but not limited to, osteoarthritis and arthritis.

BACKGROUND OF THE INVENTION

Obtaining high resolution images of joints, particularly the differentiation between bone and cartilage, can be of benefit for the diagnosis and treatment of disorders and diseases that affect joints and other regions of the body that are prone to inflammation of cartilage and other connective tissue. However, high resolution images of the boundary region between bone and cartilage can be difficult to obtain using standard imaging techniques. In addition, many imaging processes used in magnetic resonance imaging (MRI), such as in functional magnetic resonance imaging, require injections of various contrast agents in the patient either during or shortly prior to the data acquisition procedure. These injections often can cause immunologic or painful reactions and cause transient or lasting discomfort to patients.

MRI is a well-known medical imaging technique in which areas of the body are visualized via the nuclei of selected atoms, especially hydrogen nuclei. The MRI signal depends upon the environment surrounding the visualized nuclei and their longitudinal and transverse relaxation times, $T_1$ and $T_2$. Thus, in the case when the visualized nucleus is a proton, the MRI signal intensity will depend upon factors such as proton density and the chemical environment of the protons. Contrast agents are often used in MRI in order to improve the imaging contrast. They work by effecting the $T_1$, $T_2$ and/or $T_2^*$ relaxation time and thereby influence the contrast in the images.

Several types of contrast agents have been used in MRI. Blood pool MRI contrast agents, for instance superparamagnetic iron oxide particles, are retained within the vasculature for a prolonged time. They have proven to be extremely useful to enhance contrast in the liver but also to detect capillary permeability abnormalities, e.g. "leaky" capillary walls in tumors, which are a result of tumor angiogenesis.

Water-soluble paramagnetic chelates, i.e. complexes of a chelator and a paramagnetic metal ion, for instance gadolinium chelates like Omniscan™ (GE Healthcare), are widely used MR contrast agents. Because of their low molecular weight they rapidly distribute into the extracellular space when administered into the vasculature. The problem with the in vivo use of paramagnetic metal ions in a MRI contrast agent is their toxicity and therefore they are provided as complexes with chelators which are more stable and less toxic.

In addition, there is presently a need for improved and reliable methods, particularly those that are non-invasive, for detecting early stages of osteoarthritis (OA), a debilitating disease that may be triggered by injury and reflects a complex interplay of biochemical, biomedical, metabolic and genetic factors. Chan, D. D. et al., "Probing articular cartilage damage and disease by quantitative magnetic resonance imaging," Journal of Royal Society Interface 10, p. 1 (Jun. 8, 2012). The progression of OA is characterized by structural and mechanical changes in cartilage that progress from the superficial zone to the middle and then to the deep zones. Id. at p. 2. While radiography is the most common non-invasive imaging means to visualize the bone, it is not sensitive enough to detect earlier soft tissue changes. Id. Standard MRI techniques may be employed to assess changes in cartilage, including the thickness, surface area and volume. However, these measurements are nominal and may mask depth-dependent changes in cartilage, and are limited by the spatial resolution of imaging, the segmentation of regions of interest and the registration of images. Id. In addition, while standard MRI can be used to assess macroscopic changes to cartilage, it is not as sensitive to the biochemical changes associated with early stages of OA. Surowiec, R. K. et al., "Quantitative MRI in the evaluation of articular cartilage health: reproducibility and variability with a focus on T2 mapping," Knee Surg. Sports Traumatol. Arthrosc., p. 1 (Oct. 30, 2013).

Compositional imaging depends on the composition of the cartilage tissue and new techniques are being developed for segmenting cartilage and delineating margins to enhance images to show changes in the cartilage matrix. Stanton, T., "New techniques improve cartilage imaging; dGEMRIC leads pack of new biochemical methods," AAOS Now, April 2011 (http://www.aaos.org/news/aaosnow/apr11/clinical7.asp).

There is a longstanding, unmet clinical need for new and improved imaging agents, which provide high resolution imaging, decreased discomfort to the patient and increased tissue specific accumulation in the cartilage. In particular, agents that temporarily bind to the glycosaminoglycan and/or proteoglycan (e.g. chondroitin sulfate and keratin sulfate) and mucopolysaccharide constituents of cartilage (e.g. hyaluronic acid), such as those disclosed within this application, would enable the tracking of cartilage health currently inaccessible with non-invasive imaging.

SUMMARY OF THE INVENTION

The present invention is directed to a method of imaging comprising: administering to a subject in need thereof a therapeutically effective amount of a compound of formula I, II, III, IV, V, VI, VII, VIII, IX, X, XI, or XII, or a pharmaceutically acceptable salt thereof; and obtaining an image.

Another embodiment is directed to a method of diagnosing a cartilage disorder or cartilage disease comprising: administering to a subject in need thereof a therapeutically effective amount of a compound of formula I, II, III, IV, V, VI, VII, VIII, IX, X, XI, or XII, or a pharmaceutically acceptable salt thereof; obtaining an image of the subject; and diagnosing a cartilage disorder or cartilage disease from the image. A further embodiment is directed to a method of monitoring cartilage health comprising: administering to a subject in need thereof a therapeutically effective amount of a compound of formula I, II, III, IV, V, VI, VII, VIII, IX, X, XI, or XII, or a pharmaceutically acceptable salt thereof; obtaining an image of a cartilage in the subject; and quantifying the amount of the compound in the cartilage. The compounds administered in the methods of the invention may be labeled or unlabeled.

Yet another embodiment is directed to a labeled compound of formula I or a pharmaceutically acceptable salt thereof:

Y-M-X-L-A-L'-X'-M'-Y' (I)

wherein:

A is a substituted or unsubstituted aromatic or non-aromatic, carbocyclic or heterocyclic ring or a linear moiety;

L and L' are the same or different and are linkers;

X and X' are the same or different and are absent or are a functional group that attaches the linker L to M and the linker L' to M', respectively;

M and M' are the same or different and are absent or is a linker that attaches X to Y and X' to Y', respectively; and Y and Y' are the same or different and are a moiety containing one or more cationic atoms or groups or one or more groups that become cationic under physiological conditions.

In yet another embodiment of the invention, the compound is labeled di-arginine piperazine (DAP), depicted in formula V, or a related compound depicted in formula VI, or a pharmaceutically acceptable salt of either compound:

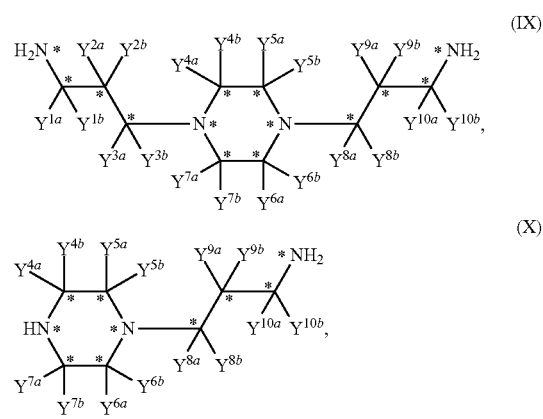

(IX)

(X)

wherein:
each Y is independently selected from hydrogen, deuterium or tritium;
each carbon denoted with an asterisk is independently selected from $^{12}C$, $^{13}C$ and $^{14}C$; and
each nitrogen denoted with an asterisk is independently selected from $^{14}N$ and $^{15}N$.

The labeled compounds may be administered in a pharmaceutical composition along with a pharmaceutically acceptable carrier.

Another embodiment is directed to a pharmaceutical composition comprising: (a) a compound of formula IX

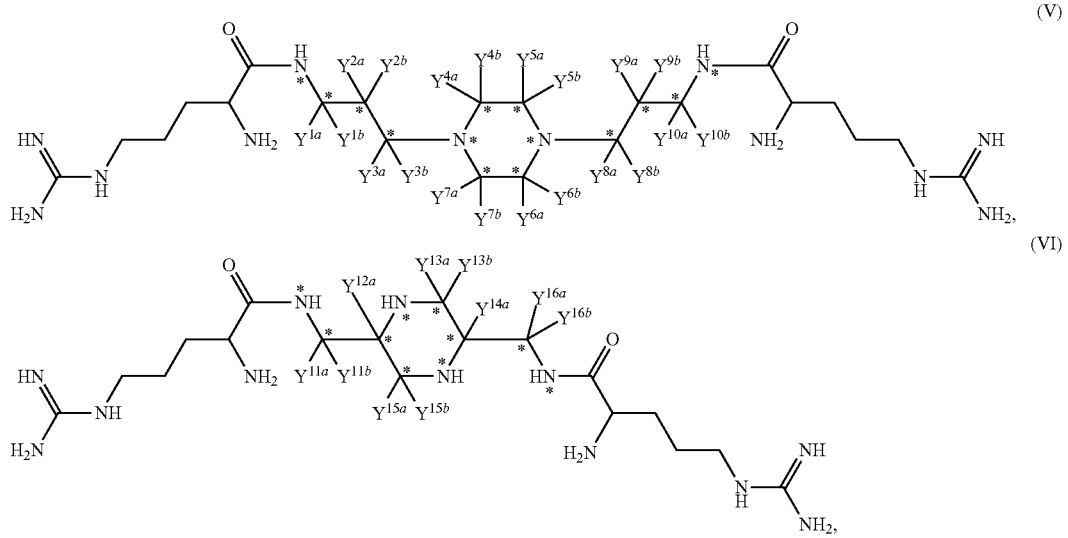

(V)

(VI)

wherein:
each Y is independently selected from hydrogen, deuterium or tritium;
each carbon denoted with an asterisk is independently selected from $^{12}C$, $^{13}C$ and $^{14}C$;
each nitrogen denoted with an asterisk is independently selected from $^{14}N$ and $^{15}N$, and
wherein at least one Y is deuterium or tritium, one carbon is $^{13}C$ or $^{14}C$, or one nitrogen is $^{15}N$.

In another specific embodiment, the present invention is directed to a metabolite of the compound of formula V as depicted in formulae IX and X:

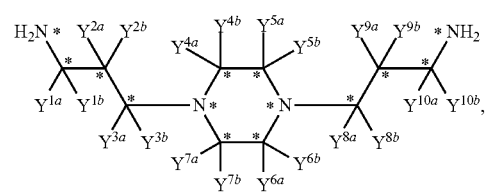

or a pharmaceutically acceptable salt thereof; and (b) a pharmaceutically acceptable carrier, wherein each Y is hydrogen, deuterium or tritium; each carbon denoted with an asterisk is $^{12}C$, $^{13}C$ or $^{14}C$; and each nitrogen denoted with an asterisk is $^{14}$N or $^{15}$N. The pharmaceutical composition may contain a compound of formula IX that is labeled, unlabeled or a combination thereof.

DETAILED DESCRIPTION OF THE INVENTION

I. Methods of Use

Figure 1:
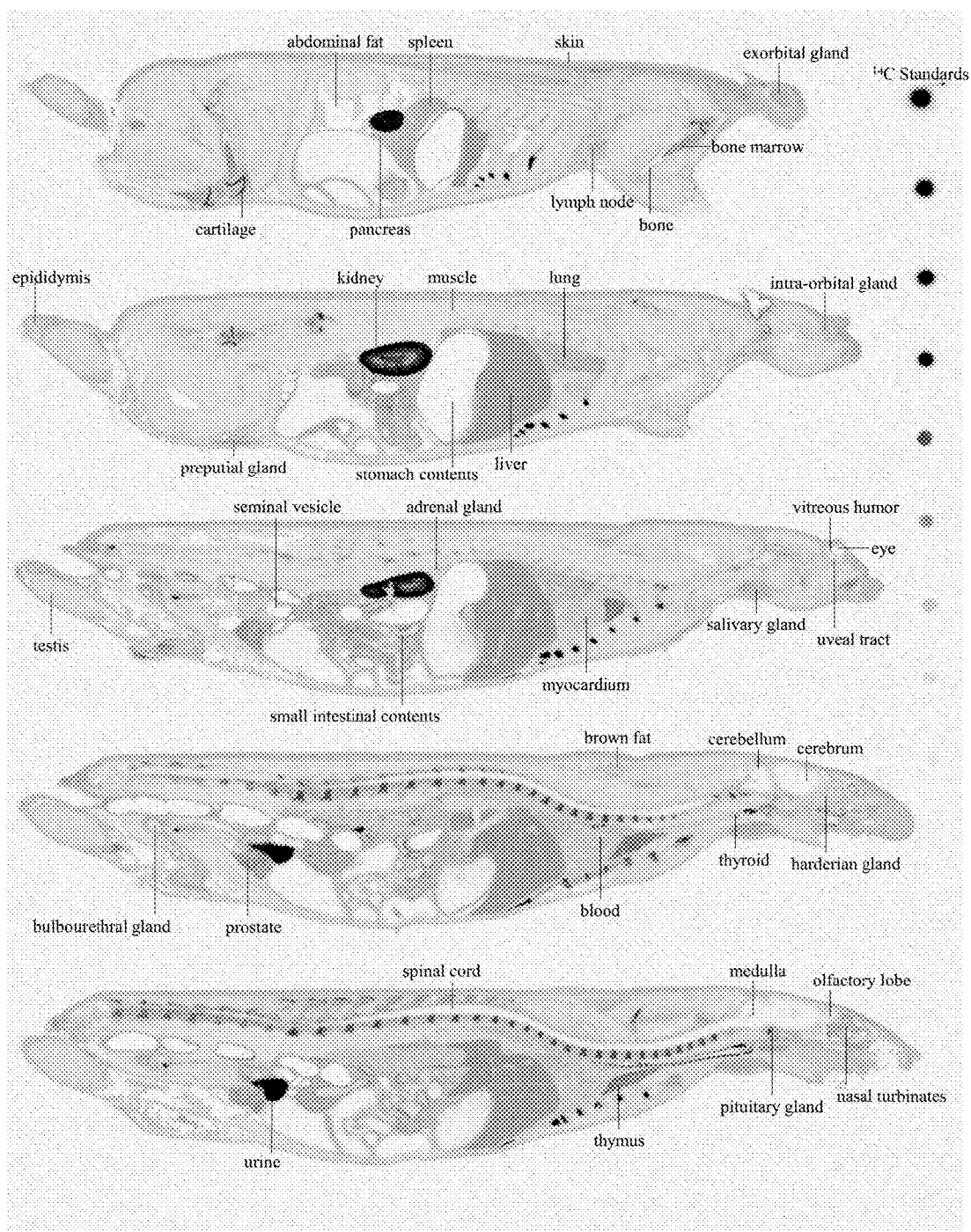
FIG. 1 is an autoradiograph taken 1 hour after a single intravenous dose of formula XIII (also referred to as [$^{14}$C] DAP) was administered to a rat by tail vein intravenous injection at a dose of about 1.8 mg/kg.
Figure 2:
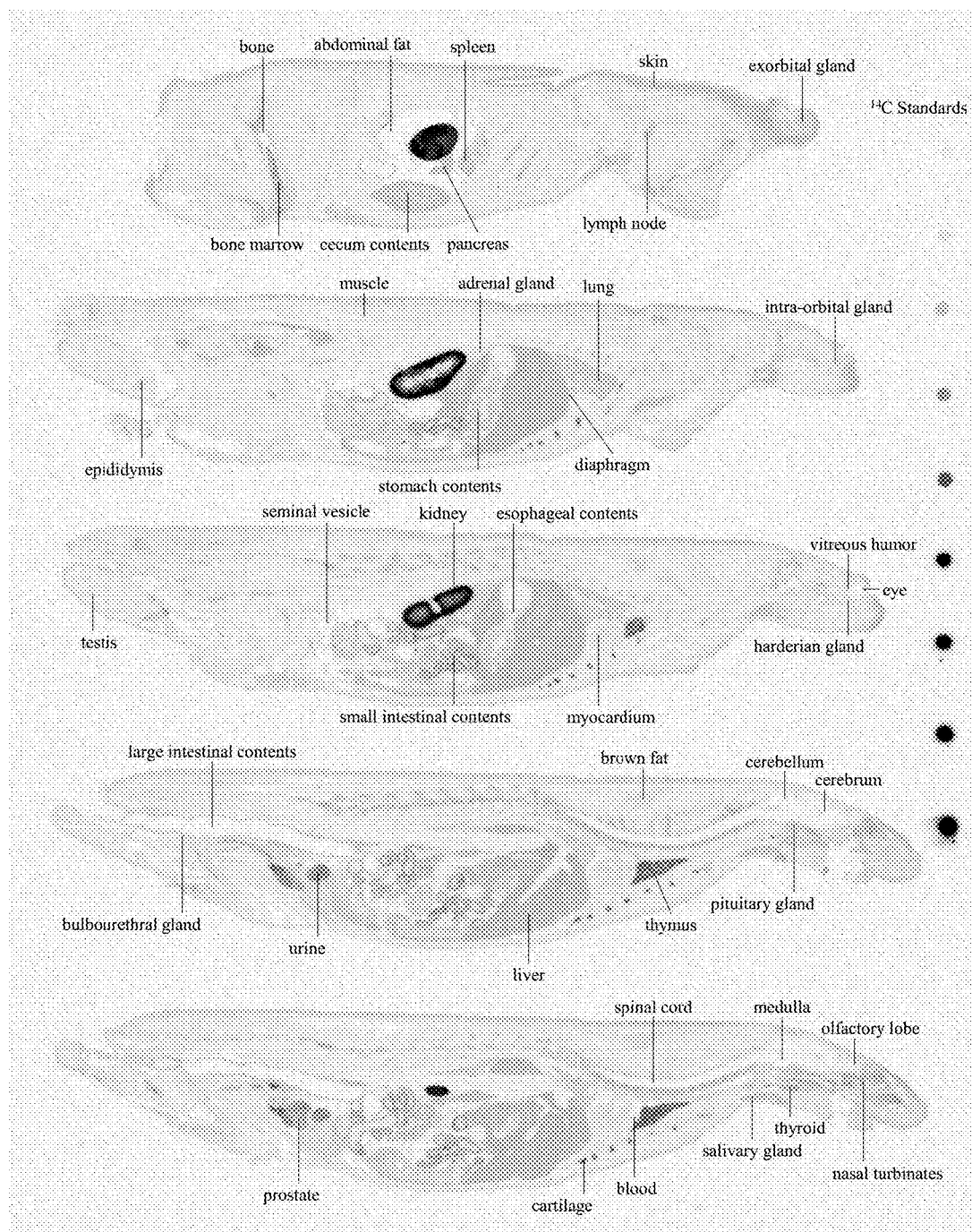
FIG. 2 is an autoradiograph taken 8 hours after a single intravenous dose of formula XIII was administered to a rat by tail vein intravenous injection at a dose of about 1.8 mg/kg.
Figure 3:
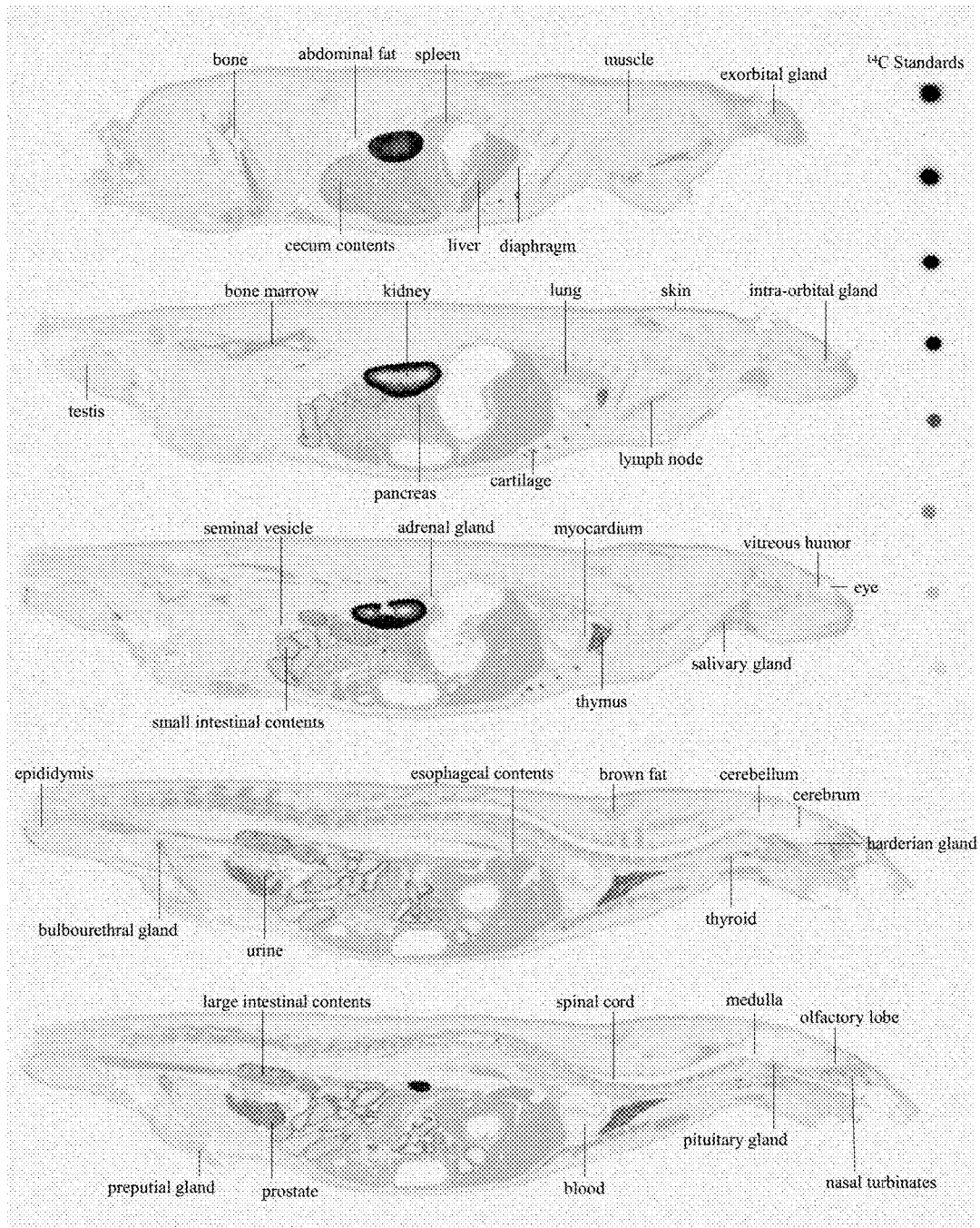
FIG. 3 is an autoradiograph taken 12 hours after a single intravenous dose of formula XIII was administered to a rat by tail vein intravenous injection at a dose of about 1.8 mg/kg.
Figure 4:
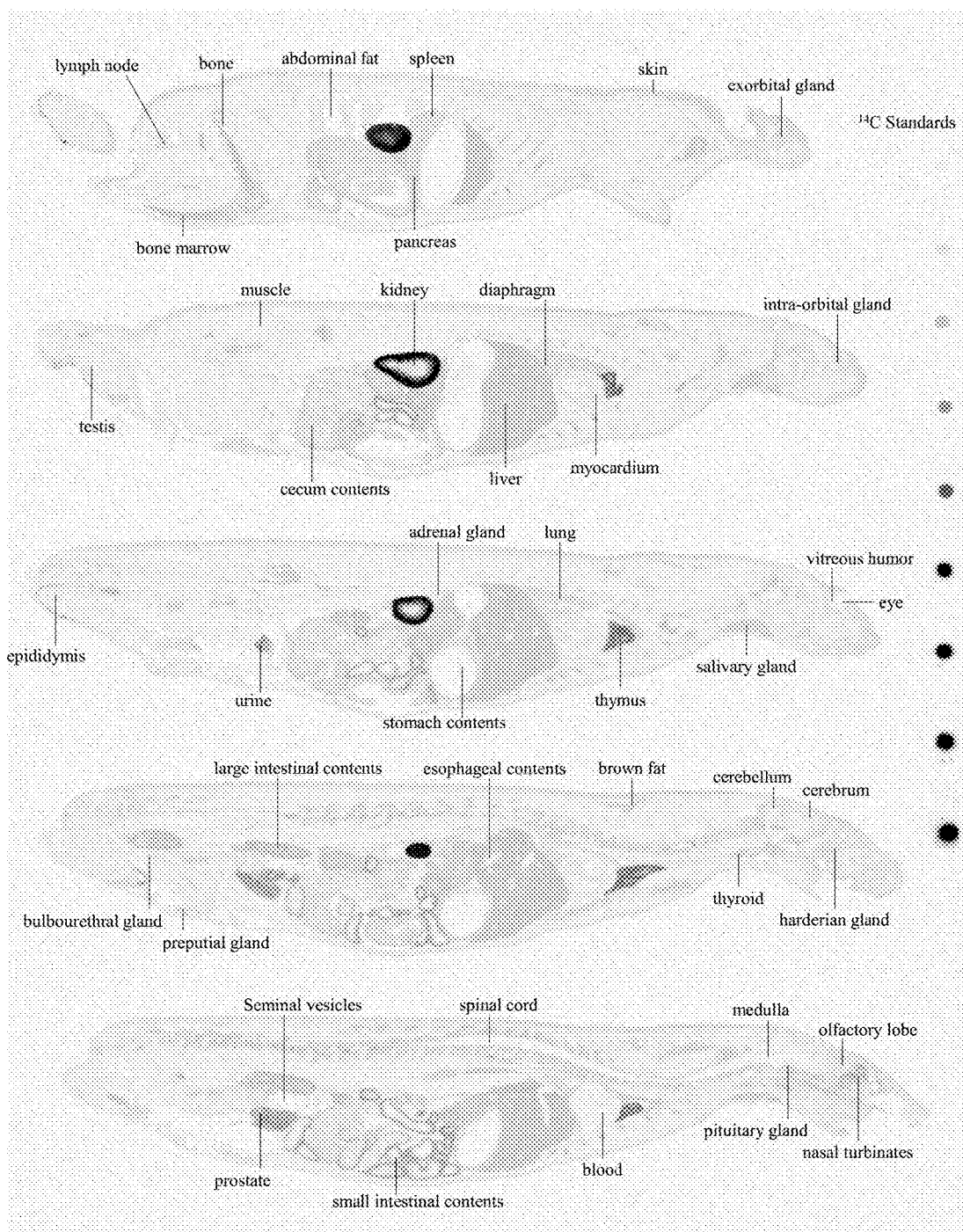
FIG. 4 is an autoradiograph taken 24 hours after a single intravenous dose of formula XIII was administered to a rat by tail vein intravenous injection at a dose of about 1.8 mg/kg.
Figure 5:
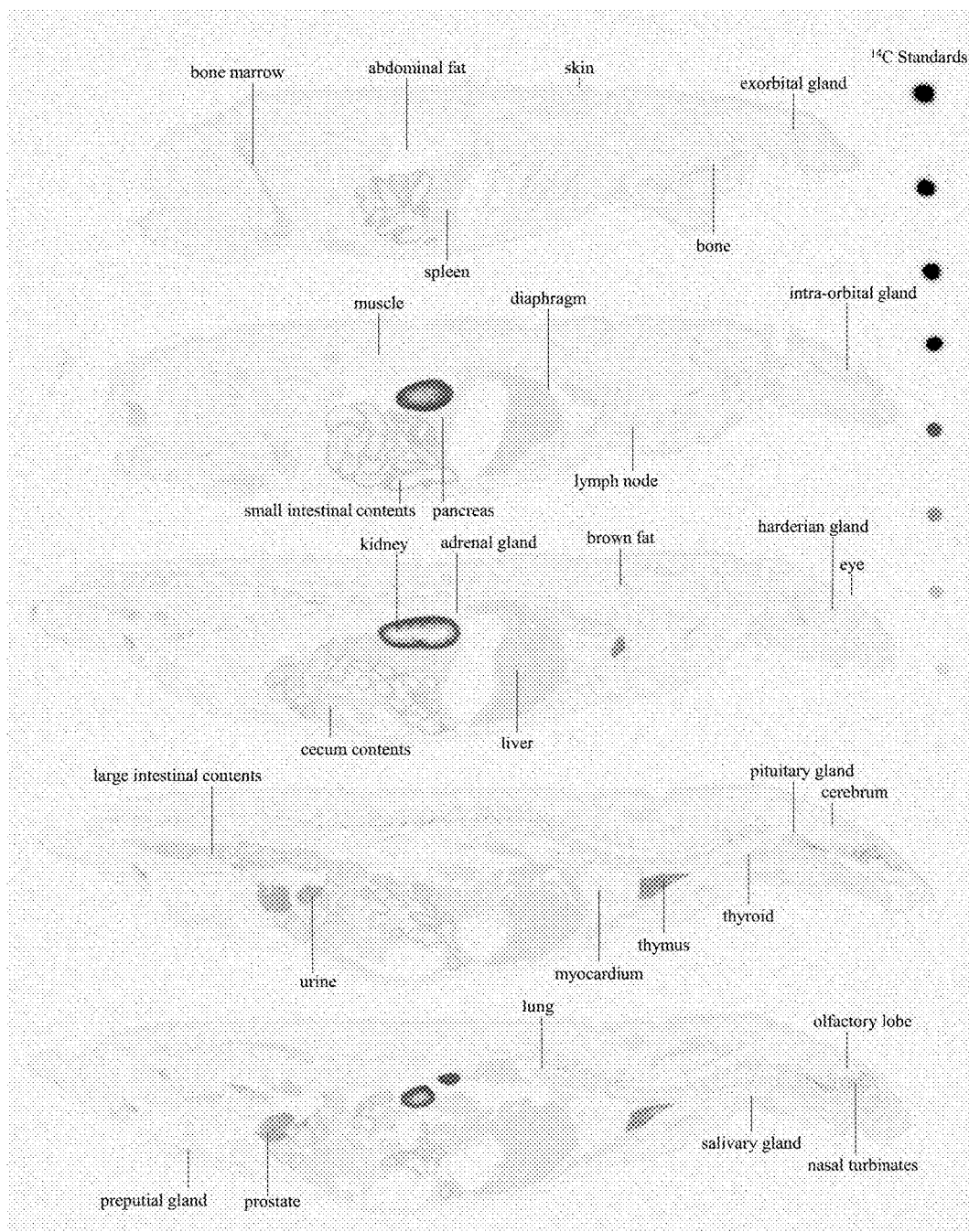
FIG. 5 is an autoradiograph taken 72 hours after a single intravenous dose of formula XIII (also referred to as [$^{14}$C] DAP) was administered to a rat by tail vein intravenous injection at a dose of about 1.8 mg/kg.

An embodiment of the present invention is directed to a method of imaging comprising: administering to a subject in need thereof a therapeutically effective amount of a compound of formula I, II, III, IV, V, VI, VII, VIII, IX, X, XI, or XII, or pharmaceutically acceptable salt thereof; and obtaining an image. In one embodiment thereof, the labeled compound of formula I, II, III, IV, V, VI, VII, VIII, IX, X, XI, or XII is administered in a method of imaging. Optionally, the labeled compound of formula I, II, III, IV, V, VI, VII, VIII, IX, X, XI, or XII and no unlabeled compound is administered in a method of imaging. In another embodiment, the unlabeled compound of formula I, II, III, IV, V, VI, VII, VIII, IX, X, XI, or XII is administered in a method of imaging. Optionally, the unlabeled compound of formula I, II, III, IV, V, VI, VII, VIII, IX, X, XI, or XII and no labeled compound is administered in a method of imaging. In yet another embodiment, both the labeled compound and unlabeled compound of formula I, II, III, IV, V, VI, VII, VIII, IX, X, XI, or XII are administered in a method of imaging.

"Labeled" as used herein refers to stable labeled or radiolabeled isotopes of the compound. This term also indicates a concentration of isotopes that is greater than a naturally occurring abundance. A stable labeled isotope or radiolabeled isotope of a compound refers to a compound wherein either: i) one or more hydrogen is replaced with deuterium or tritium; ii) one or more carbon is an isotope (i.e., $^{13}$C or $^{14}$C); or iii) one or more nitrogen is an isotope (i.e., $^{15}$N); or any combination of i, ii and iii, e.g., i and ii, i and iii, ii and iii or i, ii and iii. Further, a stable labeled compound refers to a compound containing deuterium, $^{13}$C or $^{15}$N and a radiolabeled compound (or radioisotope) refers to a compound containing tritium or $^{14}$C.

"Unlabeled" as used herein refers to a compound wherein, except as naturally occurring in nature: i) hydrogens are not replaced with deuterium or tritium; ii) each carbon is present as $^{12}$C; and iii) each nitrogen is present as $^{14}$N.

A compound of formula I is depicted as:

Y-M-X-L-A-L'-X'-M'-Y'     (I)

wherein:

A is a substituted or unsubstituted aromatic or non-aromatic, carbocyclic or heterocyclic ring or a linear moiety;

L and L' are the same or different and are linkers;

X and X' are the same or different and are absent or are a functional group that attaches the linker L to M and the linker L' to M', respectively;

M and M' are the same or different and are absent or is a linker that attaches X to Y and X' to Y', respectively; and Y and Y' are the same or different and are a moiety containing one or more cationic atoms or groups or one or more groups that become cationic under physiological conditions. As previously described, the compound of formula I may be labeled or unlabeled when used in the methods of the invention. In addition, an embodiment of the invention includes the labeled compounds of formula I.

The compound can be symmetrical or asymmetrical; that is, one or more of L, L', X, X', M, M', Y, or Y' can be the same or different. The compound can be chiral (i.e., contain one or more chiral centers) or achiral.

In some embodiments, A is a heterocyclic moiety. In other embodiments, A is a heterocyclic moiety and L and L' are a substituted or unsubstituted alkylene chain. In still other embodiments, A is a heterocyclic moiety, L and L' are a substituted or unsubstituted alkylene chain, and X and X' are —NH—C(=O)—. In still other embodiments, A is a heterocyclic moiety, L and L' are a substituted or unsubstituted alkylene chain, X and X' are —NH—C(=O)—, and M and M' are a substituted alkylene chain. As used herein, alkylene chain is a divalent alkelene moiety that is $C_1$ to $C_{10}$, preferably $C_3$ to $C_6$ in length, and which may be substituted or unsubstituted. Exemplary substituents include alkyl, hydroxyl, hydroxyl alkyl, amino, amino alkyl, alkoxy, alkyl alkoxy. As used herein, the term alkyl is $C_1$ to $C_{10}$, preferably $C_1$-$C_6$ straight chain or branched hydrocarbon. In still other embodiments, A is a heterocyclic moiety, L and L' are a substituted or unsubstituted alkylene chain, X is —NH—C(=O)—, M and M' are a substituted alkylene chain, and Y and Y' are a guanidine moiety.

In some embodiments, A is a non-aromatic, heterocyclic ring, such as piperazine or diketopiperazine. In other embodiments, A is a linear moiety, such as a linear diamine or other linear moiety containing reactive functional groups that can form a bond to X and X', when present, or Y and Y'. In some embodiments, the linkers L and L' are attached to the heteroatoms in the ring A, such as the two nitrogen atoms in piperazine. In other embodiments, the linker L and L' are attached to atoms other than the heteroatoms in the ring, such as carbon. In particular embodiments, A is a 1,4 or 2,5 disubstituted piperazine ring. In some embodiments, L and L' and/or M and M' are a substituted or unsubstituted alkylene chains, such as —(CH$_2$)$_n$—, where n is an integer from 1-10, preferably from 1-6, e.g., 1-3. In particular embodiments, n is 3. In some embodiments, L and/or M are absent.

X and X' are a functional group that attaches the linkers L and L' to Y and Y'. Exemplary functional groups include, but are not limited to, esters, amides, carbonates, and ketones. In particular embodiments, X and X' are a functional group that is resistant to simple hydrolysis, such as an amide group.

Y and Y' are a moiety that contains one or more atoms or groups that are cationic or will be cationic under physiological conditions. Examples include amine and guanidine moieties as well as phosphorous containing moieties, such as alkyltriphenylphosphonium, tetraphenylphosphonium, tetraphenylarsonium, tribenzyl ammonium, and phosphonium moieties. Additional cationic moieties include cationic oligomers and polymers, such as oligo- or polylysine, oligo- or polyarginine, N-alkylated polyethylene imine, and the like. Other cationic moieties include delocalized lipophilic cations containing one to three carbimino, sulfimino, or phosphinimino units as described in Kolomeitsev et al., *Tet. Let.*, Vol. 44, No. 33, 5795-5798 (2003).

In some embodiments, the compound is a piperazine derivative, wherein the amino acid side chains contain one or more positively charged atoms or atoms that will be positively charged under physiological conditions. Examples include diarginine piperazine. Other amino acids that are positively charged or will be positively charged under physiological conditions can be substituted for arginine.

"Aromatic", as used herein, refers to 5-12-membered, preferably 5-, 6- and 7-membered aromatic, heterocyclic, fused aromatic, fused heterocyclic, biaromatic, or biheterocyclic ring systems, optionally substituted. Broadly defined, "Ar", as used herein, includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "Ar" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(R) wherein R is absent or is H, O, (C$_{1-4}$)alkyl, phenyl or benzyl, and optionally containing 1-3 double bonds and optionally substituted with one or more substituents. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

A compound of formula II is depicted as:

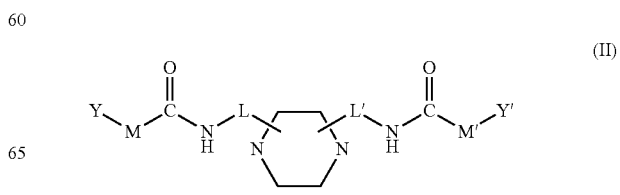

wherein each of L, L', M, M', Y and Y' are as previously described. The compound of formula II may be labeled or unlabeled when used in the methods of the invention. In addition, an embodiment of the invention includes the labeled compounds of formula II.

A compound of formula III is depicted as:

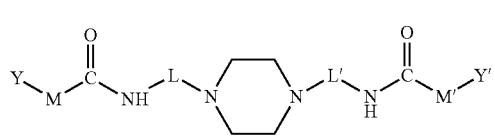
(III)

wherein L, L', M, M', Y and Y' are as previously described. The compound of formula III may be labeled or unlabeled when used in the methods of the invention. In addition, an embodiment of the invention includes the labeled compounds of formula III.

A compound of formula IV is depicted as:

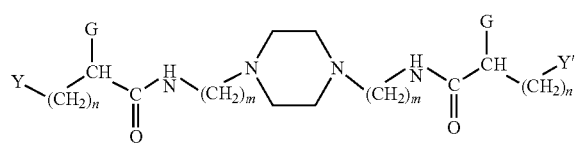
(IV)

wherein Y and Y' are as previously described and n is 3 to 5, m is 3 to 6 and G is selected from —NH$_2$ and OH. Most preferably, G is amino. The compound of formula IV may be labeled or unlabeled when used in the methods of the invention. In addition, an embodiment of the invention includes the labeled compounds of formula IV.

In the compound of any of formula II, III or IV, Y and Y' may be independently selected from the group consisting of

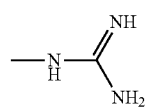

and —NH$_2$. Most preferably, G is —NH$_2$ and Y and Y' are

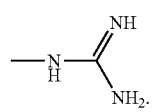

In one embodiment, a method of imaging comprises administering di-arginine piperazine ("DAP"), the compound of formula V, or a related compound of formula VI, or a pharmaceutically acceptable salt of either compound:

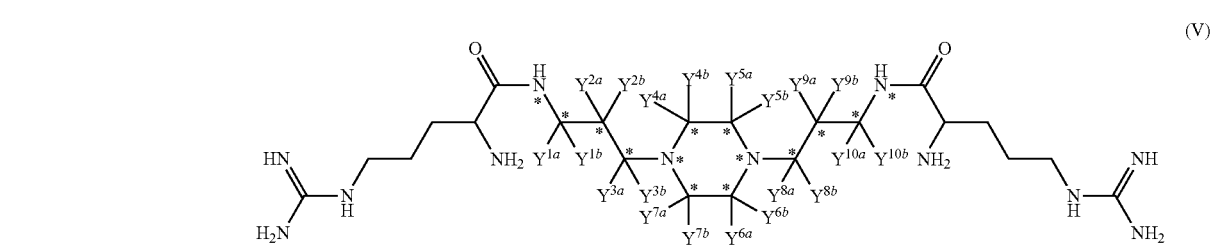
(V)

2-Amino-5-guanidino-pentanoic acid (3-{4-[3-(2-amino-5-guanidino-pentanoylamino)-propyl]-piperazin-1-yl}-propyl)-amide; or

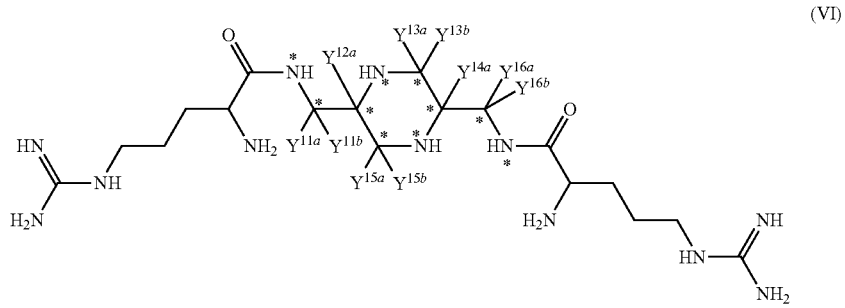
(VI)

2-Amino-5-guanidino-pentanoic acid {5-[(2-amino-5-guanidino-pentanoylamino)-methyl]-piperazin-2-ylmethyl}-amide,
wherein:
each Y is independently selected from hydrogen, deuterium or tritium;
each carbon denoted with an asterisk is independently selected from $^{12}C$, $^{13}C$ and $^{14}C$; and
each nitrogen denoted with an asterisk is independently selected from $^{14}N$ and $^{15}N$.

The compound of formula V or VI may be labeled or unlabeled. Another embodiment of the invention is the compound of formula V or VI when labeled. In that embodiment, at least one Y is deuterium or tritium, and/or at least one carbon is $^{13}C$ or $^{14}C$, and/or at least one nitrogen is $^{15}N$. In an embodiment, at least one Y is deuterium. In another embodiment, at least one Y is deuterium, each carbon is $^{12}C$ and each nitrogen is $^{14}N$.

When the compound of formula V or VI is unlabeled, each Y is hydrogen, each carbon is $^{12}C$, and each nitrogen is $^{14}N$, depicted as follows in formulae V* and VI*, respectively:

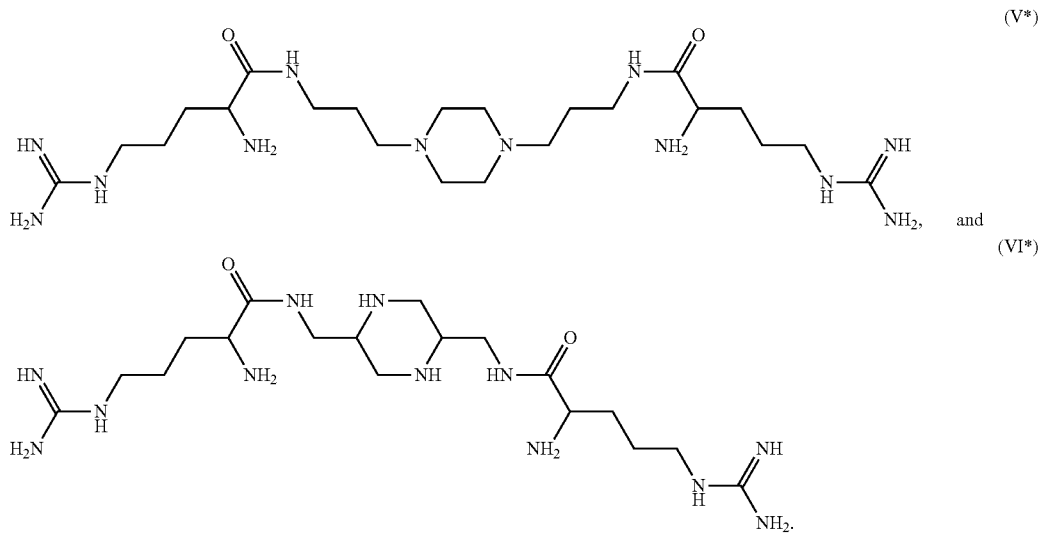

In one embodiment, the labeled compound of formula V is administered in a method of imaging. Optionally, in that method of imaging, no unlabeled compound of formula V is also administered. In another embodiment, the unlabeled compound of formula V is administered in a method of imaging. Optionally, in that method of imaging, no labeled compound of formula V is also administered. In yet another embodiment, both the labeled compound and the unlabeled compound of formula V are administered in a method of imaging.

In one embodiment, the labeled compound of formula VI is administered in a method of imaging. Optionally, in that method of imaging, no unlabeled compound of formula VI is also administered. In another embodiment, the unlabeled compound of formula VI is administered in a method of imaging. Optionally, in that method of imaging, no labeled compound of formula VI is also administered. In yet another embodiment, both the labeled compound and the unlabeled compound of formula VI are administered in a method of imaging.

The compound of formula VII is a stereoisomer as depicted of formula V:

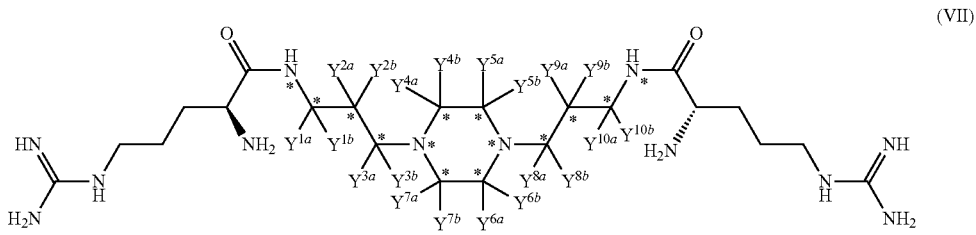

wherein:
  each Y is independently selected from hydrogen, deuterium or tritium;
  each carbon denoted with an asterisk is independently selected from $^{12}C$, $^{13}C$ and $^{14}C$; and
  each nitrogen denoted with an asterisk is independently selected from $^{14}N$ and $^{15}N$.

The compound of formula VIII is a stereoisomer of formula VI:

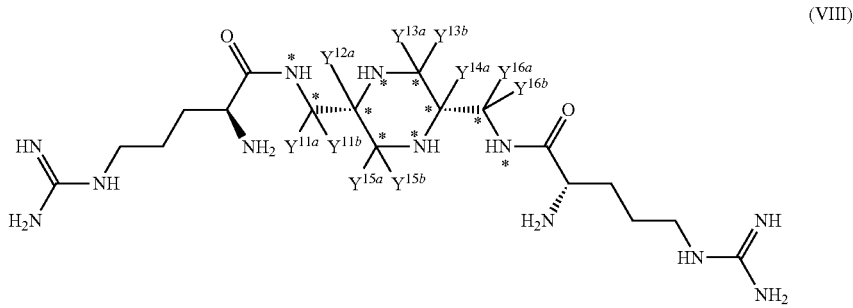

(VIII)

wherein:
  each Y is independently selected from hydrogen, deuterium or tritium;
  each carbon denoted with an asterisk is independently selected from $^{12}C$, $^{13}C$ and $^{14}C$; and
  each nitrogen denoted with an asterisk is independently selected from $^{14}N$ and $^{15}N$.

The compound of formula VII or VIII may be labeled or unlabeled. Another embodiment of the invention is the compound of formula VII or VIII when labeled In that embodiment, at least one Y is deuterium or tritium, and/or at least one carbon is $^{13}C$ or $^{14}C$, and/or at least one nitrogen is $^{15}N$. In a certain embodiment, at least one Y is deuterium. In another embodiment, at least one Y is deuterium, each carbon is $^{12}C$ and each nitrogen is $^{14}N$.

When the compound of formula VII or VIII is unlabeled, each Y is hydrogen, each carbon is $^{12}C$, and each nitrogen is $^{14}N$, depicted as follows in formulae VII* and VIII*, respectively:

In an embodiment, a method of imaging comprises administering a compound of formula VII or formula VIII, or a pharmaceutically acceptable salt of either compound. In one embodiment, the labeled compound of formula VII is administered in a method of imaging. Optionally, in that method of imaging, no unlabeled compound of formula VII is also administered. In another embodiment, the unlabeled compound of formula VII is administered in a method of imaging. Optionally, in that method of imaging, no labeled compound of formula VII is also administered. In yet another embodiment, both the labeled compound and the unlabeled compound of formula VII are administered in a method of imaging. In one embodiment, the labeled compound of formula VIII is administered in a method of imaging. Optionally, in that method of imaging, no unlabeled compound of formula VIII is also administered. In another embodiment, the unlabeled compound of formula VIII is administered in a method of imaging. Optionally, in that method of imaging, no labeled compound of formula VIII is also administered. In yet another embodiment, both the labeled compound and the unlabeled compound of formula VIII are administered in a method of imaging.

The synthesis of the compounds of formulae I, II, III, IV, V, VI, VII and VIII, which are disclosed for use as anticoagulant reversal agents, is taught in commonly-assigned U.S. Patent Application Publication No. 2013/0137702, the contents of which are hereby incorporated by reference in their entirety.

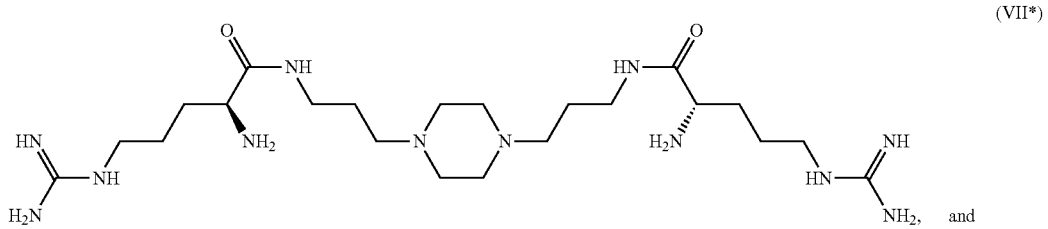

(VII*)

and

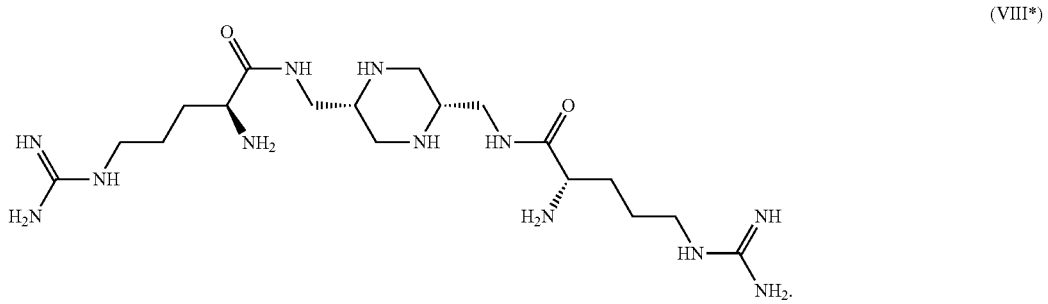

(VIII*)

In certain embodiments, the labeled compound of formulae V, VI, VII or VIII has more than one of $Y^{4a}$, $Y^{4b}$, $Y^{5a}$, $Y^{5b}$, $Y^{6a}$, $Y^{6b}$, $Y^{7a}$, and $Y^{7b}$ being deuterium or tritium. In an embodiment thereof, all of $Y^{4a}$, $Y^{4b}$, $Y^{5a}$, $Y^{5b}$, $Y^{6a}$, $Y^{6b}$, $Y^{7a}$, and $Y^{7b}$ are deuterium. In another embodiment, $Y^{4a}$, $Y^{4b}$, $Y^{5a}$, $Y^{5b}$, $Y^{6a}$, $Y^{6b}$, $Y^{7a}$, and $Y^{7b}$ are deuterium and all of the carbons in the labeled compound are $^{12}C$ and all of the nitrogens are $^{14}N$.

Another embodiment is a method of imaging comprising: administering to a subject in need thereof a therapeutically effective amount of a compound or a pharmaceutically acceptable salt thereof selected from the group consisting of:

formula V, 1,4-bis(3-amino propyl) piperazine (BAP) and mono-arginine piperazine (MAP), distribute well to cartilage and tissues. The compound of formula IX, X, XI or XII may be labeled or unlabeled.

When the compound of any one of formulae V, VI, VII, VIII, IX, X, XI, or XII is unlabeled, each Y is hydrogen, each carbon is $^{12}C$, and each nitrogen is $^{14}N$. When the compound of any one of formulae V, VI, VII, VIII, IX, X, XI, or XII is labeled, at least one Y is deuterium or tritium, or carbon is $^{13}C$ or $^{14}C$, or nitrogen is $^{15}N$. In a certain embodiment, at least one Y is deuterium. In another embodiment, at least one Y is deuterium, each carbon is $^{12}C$ and each nitrogen is $^{14}N$.

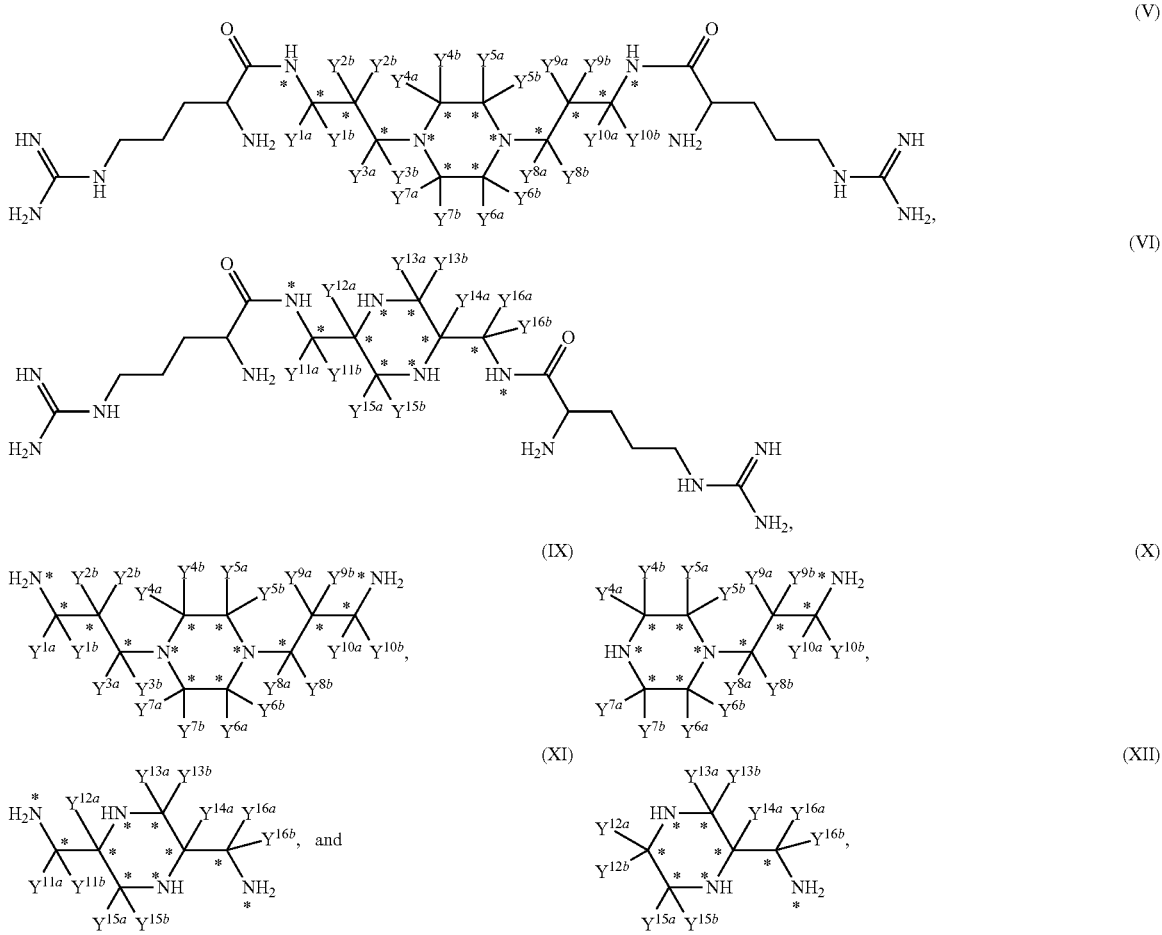

wherein:
each Y is independently selected from hydrogen, deuterium or tritium;
each carbon denoted with an asterisk is independently selected from $^{12}C$, $^{13}C$ and $^{14}C$; and
each nitrogen denoted with an asterisk is independently selected from $^{14}N$ and $^{15}N$; and
obtaining an image. As previously described, the compounds used in the method of imaging may be labeled, unlabeled or a combination thereof. Embodiments of the invention include the labeled compounds of V, VI, IX, X, XI, XII described above, and also the unlabeled compounds of IX, X, XI, XII.

Formulae IX and X are metabolites of formula V, and formulae XI and XII are metabolites of formula VI. For example, it is believed that the primary metabolites of In one embodiment, the labeled compound of any one of formulae V, VI, VII, VIII, IX, X, XI, or XII is administered in a method of imaging. Optionally, in that method of imaging, no unlabeled compound of any one of formulae V, VI, VII, VIII, IX, X, XI, or XII is also administered. In another embodiment, the unlabeled compound of any one of formulae V, VI, VII, VIII, IX, X, XI, or XII is administered in a method of imaging. Optionally, in that method of imaging, no labeled compound of any one of formulae V, VI, VII, VIII, IX, X, XI, or XII is also administered. In yet another embodiment, both the labeled compound and the unlabeled compound of any one of formulae V, VI, VII, VIII, IX, X, XI, or XII are administered in a method of imaging.

In certain embodiments of formulae V, VI, VII, VIII, IX, X, XI, or XII, when labeled, the labeling is in the central moiety of the above described compounds, and preferably the piperazine, because the arginine gets metabolized by the body.

Preferably, the method of imaging may comprise administering a compound of formulae V, VI or IX, or a pharmaceutically acceptable salt thereof. In one embodiment, the labeled compound of formulae V, VI or IX is administered in a method of imaging. Optionally, in that method of imaging, no unlabeled compound of formulae V, VI or IX is also administered. In another embodiment, the unlabeled compound of formulae V, VI or IX is administered in a method of imaging. Optionally, in that method of imaging, no labeled compound of formulae V, VI or IX is also administered. In yet another embodiment, both the labeled compound and the unlabeled compound of formulae V, VI or IX are administered in a method of imaging.

In another embodiment, the method of imaging comprises administering a compound of formula IX, or a pharmaceutically acceptable salt thereof. In one embodiment, the labeled compound of formula IX is administered in a method of imaging. Optionally, in that method of imaging, no unlabeled compound of formula IX is also administered. In another embodiment, the unlabeled compound of formula IX is administered in a method of imaging. Optionally, in that method of imaging, no labeled compound of formula IX is also administered. In yet another embodiment, both the labeled compound and the unlabeled compound of formula IX are administered in a method of imaging.

The phrase "pharmaceutically acceptable salt" of a compound as used herein means a salt that is pharmaceutically acceptable and that possesses the desired pharmacological activity of the parent compound. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Suitable base salts include, but are not limited to, aluminum, calcium, lithium, magnesium, potassium, sodium, zinc, and diethanolamine salts.

Imaging, or "medical imaging," is the technique and process used to create images of the body (or parts and function thereof) for clinical purposes (e.g., medical procedures seeking to reveal, diagnose, or examine disease) or medical science (including the study of normal anatomy and physiology). Imaging includes biological imaging and incorporates Radiology, Magnetic Resonance Imaging, Nuclear medicine, medical Ultrasonography or Ultrasound, Endoscopy, Elastography, Tactile Imaging, Thermography and medical photography. In an embodiment, the image is obtained using radiography or magnetic resonance imaging (MRI). Preferably, the magnetic resonance imaging is chemical shift imaging.

Radiography is the use of X-rays to view a non-uniformly composed material (i.e., of varying density and composition) such as the human body. Two forms of radiographic images are used in medical imaging; projection radiography and fluoroscopy, with the latter being useful for catheter guidance. These 2D techniques are still in wide use despite the advance of 3D tomography because of the low cost, high resolution, and depending on application, lower radiation dosages.

Magnetic resonance imaging (MRI) is a test that uses a magnetic field and pulses of radio wave energy to make pictures of organs and structures inside the body. A conventional magnetic resonance imaging instrument (MRI scanner) uses powerful magnets to polarize and excite hydrogen nuclei (single proton) in water molecules in human tissue, producing a detectable signal which is spatially encoded, resulting in images of the body. The MRI machine emits an RF (radio frequency) pulse that specifically binds only to hydrogen. The system sends the pulse to the area of the body to be examined. The pulse makes the protons in that area absorb the energy needed to make them spin in a different direction. Thus, conventional MRI, may also be referred to as 1H MRI. Modern MRI instruments are capable of producing images in the form of 3D blocks, which may be considered a generalization of the single-slice, tomographic, concept.

In certain embodiments, in MRI imaging, after administration of a compound to the subject, the presence of the compound increases the signal to noise ratio at the site of interest, for example, the cartilage, organ, smooth muscle fiber, or a tissue, by at least about a factor of two. Signal to noise ratio is readily understood by one of ordinary skill in the art. See Redpath, T. W., "Signal-to-noise ratio in MRI," The British Journal of Radiology, Vol. 71, pp. 704-707 (1998); and Parrish, T. B., "Impact of signal-to-noise on functional MRI," Magnetic Resonance in Medicine, Vol. 44, pp. 924-932 (2000).

Chemical shift imaging MRI, or simply "chemical shift imaging," is the process of mapping the spatial distribution of nuclei associated with a particular chemical shift (e.g., hydrogen nuclei associated with water or with lipid groups). Brateman, L., "Chemical Shift Imaging: A Review," Am. J. Roentgenol., Vol. 146, No. 5, pp. 971-980, 972 (1986). Chemical shifts are seen when an isotope possessing a nuclear magnetic dipole moment resonates at a spectrum of resonance frequencies in a given magnetic field. Id. Thus, rather than imaging the entire spectrum of resonance frequencies within the body, chemical shift imaging may be used to view the spatial distribution of nuclei having a particular resonance frequency. Id. Chemical shift imaging acquires the proton spectra over a range of resonance frequency or a single resonance frequency to generate a three-dimensional spatial distribution of the imaging agent in the imaged tissue or tissues. The chemical shift image can be overlaid with standard proton magnetic resonance imaging to correlate the distribution of the imaging agent with the native tissue morphology. Chemical shift imaging may be better suited to certain types of imaging and diagnosis than conventional MRI.

In an aspect of the invention, stable labeled compounds and unlabeled compounds are used as imaging agents for MRI and radiolabeled compounds are used as imaging agents for radio-imaging, such as radiography.

As used herein, "subject in need thereof" is a subject in need of obtaining an image of, for example, a cartilage, an organ, a smooth muscle fiber, and/or a tissue for detection or assessment of any disease, ailment or condition.

The "subject", as used herein, is an animal. In one embodiment, the subject is a mammal. In another embodiment, the subject is a human.

As used herein, "therapeutically effective amount" refers to an amount of a compound of formulae I, II, III, IV, V, VI, VII, VIII, IX, X, XI, or XII (i.e., an imaging agent), which is effective, upon single or multiple dose administration (e.g., bolus and/or maintenance doses) to a subject, in localizing and residing in a cartilage, an organ, a smooth muscle fiber, and/or a tissue. Therapeutically effective is also intended to refer to an amount of the compound suitable for diagnostic uses. If the compound used in the method of the invention is labeled, the therapeutically effective amount may be dependent on the extent of labeling of the compound.

In one embodiment of the invention, a therapeutically effective amount of the compounds described herein may be administered by subcutaneous, intramuscular, or intravenous route of administration. For example, it may be administered intravenously as a sterile solution. In another embodiment, a therapeutically effective amount of the imaging agent is administered by oral, nasal, or pulmonary route, or to a mucosal region (mouth, rectum, or vagina). In a preferred embodiment thereof, the compounds described herein may be administered intravenously, intra-articularly or orally.

The therapeutically effective amount of the compounds described herein will typically range from about 0.001 mg/kg to about 1 g/kg of body weight per day; in another embodiment, from about 0.01 mg/kg to about 600 mg/kg body weight per day; in another embodiment, from about 0.01 mg/kg to about 250 mg/kg body weight per day; in another embodiment, from about 0.01 mg/kg to about 400 mg/kg body weight per day; in another embodiment, from about 0.01 mg/kg to about 200 mg/kg of body weight per day; in another embodiment, from about 0.01 mg/kg to about 100 mg/kg of body weight per day; in one embodiment, from about 0.01 mg/kg to about 25 mg/kg body weight per day; in another embodiment, from about 0.1 mg/kg to about 10 mg/kg body weight per day; in another embodiment, from about 0.001 mg/kg to about 100 mg/kg of body weight per day; in another embodiment, from about 0.001 mg/kg to about 10 mg/kg of body weight per day; and in another embodiment, from about 0.001 mg/kg to about 1 mg/kg of body weight per day.

In a certain embodiment of the invention, the therapeutically effective amount of the compound used in the methods of the invention is about 0.001 mg/kg to about 1 g/kg of body weight per day and the compound or pharmaceutically acceptable salt thereof is administered intravenously, intra-articularly or orally. Preferably, the compound or pharmaceutically acceptable salt thereof may be administered intravenously or orally.

In another embodiment, the method of imaging comprises administering a therapeutically effective amount of the compounds described herein or pharmaceutically acceptable salt to a subject in need thereof, and obtaining an image of a cartilage, an organ, a smooth muscle fiber, and/or a tissue of the subject.

In yet another embodiment, the method of imaging using the compounds described herein further comprises assessing osteoarthritis by tracking proteoglycan and glycosaminoglycan content of cartilage from the image. Preferably, cartilage may be selected from the group consisting of hyaline cartilage, fibrocartilage and elastic cartilage, and preferably, may be hyaline cartilage. The compounds disclosed herein (e.g., DAP) are capable of binding heparin, inactivating it in vivo. Heparin is a naturally occurring mucopolysaccharide that acts in the body as an antithrombin co-factor to prevent intravascular clotting. The substance is produced by basophils and mast cells, which are found in large numbers in the connective tissue surrounding capillaries, particularly in the lungs and liver. In the form of sodium salt, heparin is used therapeutically as an anticoagulant. Thus, because heparins are a class of proteoglycans found in cartilage, a compound of the invention, i.e., a labeled compound described herein, or a non-labeled compound described herein, may also be used to track the progression of proteoglycan and glycosaminoglycan content of cartilage as they are early markers of osteoarthritis. Therefore, a method of imaging of the present invention may assess osteoarthritis in both early stage and late stage development.

An embodiment is directed to the method of imaging, further comprising diagnosing a growth disorder (e.g., achondroplasia) from the image.

The image may also be a urogram which may be used to detect non-stone defects in the kidney, bladder, ureters, as well as to avoid cystograms, where one could likely quantitate residual volumes, etc.

DAP non-covalently binds to heparins, as taught in commonly-assigned U.S. Patent Application Publication No. 2013/0137702, which are a constituent of the proteoglycan portion of cartilage and are molecularly similar to the glycosaminoglycan portion of cartilage. As such, DAP and its pharmaceutically acceptable salts and metabolites can be used to image the proteoglycan, glycosaminoglycan and mucopolysaccharide content of cartilage as a marker of cartilage health. Since DAP binds proteoglycans, glycasominoglycans, and mucopolysaccharides for a period of hours, the amount of DAP detected in the cartilage correlates to the proteoglycan and glycosaminoglycan content. Proteoglycan and glycosaminoglycan loss in hyaline cartilage is an early sign of osteoarthritis and therefore DAP (labeled or non-labeled) and its pharmaceutically acceptable salts and metabolites can be used as imaging agents for tracking cartilage health.

Cartilage refers to any flexible connective tissue found in the subject, including, for example in humans, the joints between bones, the rib cage, the ear, the nose, the bronchial tubes and the intervertebral discs. In a certain embodiment, a method of the present invention comprises obtaining an image of a cartilage selected from the group consisting of hyaline cartilage, fibrocartilage and elastic cartilage. In a preferred embodiment, the method comprises obtaining an image of hyaline cartilage.

The image may be of urine or any organ, including but not limited to the cartilage, kidneys, urinary bladder, thymus, gastrointestinal tract, bone marrow and prostate. Also the image may be of a gland, including but not limited to the adrenal, salivary, thymus, prostate, harderian, pituitary, bulbourethral, exorbital and mammary gland.

The image may be of any smooth muscle fiber, including but not limited to the ureters.

The image may be of any tissue in the subject, including but not limited to the cartilage, kidneys, urinary bladder, thymus, gastrointestinal tract, bone marrow, liver, prostate, salivary glands, lymph nodes, pituitary gland, preputial gland, spleen, extraorbital glands, lungs, intraorbital glands, nasal turbinates, skin, pancreas, thyroid, fat, uveal tract, epididymis, myocardium, blood, diaphragm, adrenal glands testes, muscles, bone and spinal cord.

In an embodiment, the image is of the prostate, thymus, kidney, ureter and/or bladder. In another embodiment, the image is of a cartilage and the method further comprises tracking a proteoglycan and glycosaminoglycan content of the cartilage. Proteoglycan and glycosaminoglycan content of cartilage are early markers for assessing osteoarthritis.

In an embodiment, the compound administered in a method of imaging localizes in cartilage, an organ, a smooth muscle fiber, and/or a tissue of the subject, and in another embodiment, localizes in the prostate, thymus, kidney, ureter and bladder. The clinical benefit of the compound used as an imaging agent depends on its ability to localize in a region of interest, such as in cartilage, an organ, a smooth muscle fiber, and/or a tissue. Localization of the imaging agent is its ability to target a region of interest, such as in cartilage, an organ, a smooth muscle fiber, and/or a tissue, and reside in that location to allow for imaging. Localization may be controlled in several ways, including: i) bolus timing, ii) molecular size and type of the imaging agent (e.g., larger molecules remain with blood vessels, while smaller molecules disperse into extracellular fluid compartments), iii) the presence of any special moieties in the imaging agent that selectively bind to tissue, iv) means of administration, v) total dose administered, and vi) dosing schedule. See Ersoy, H. et al., "Contrast Agents for Cardiovascular MRI," *Cardiovascular Magnetic Resonance Imaging*, R. Kwong, ed., Humana Press Inc., Chapter 10, p. 239 (2008).

In another embodiment, the compound administered in a method of imaging has a residence time of about 1 hour to about 100 hours, preferably a residence time of about 1 hour to about 72 hours, more preferably a residence time of about 1 hour to about 42 hours, still more preferably a residence time of about 1 hour to about 24 hours, and most preferably a residence time of about 5 hours to about 15 hours, in the region in which the compound localizes. Residence time is the average amount of time that the compound, used as an imaging agent, remains in the localized region, such as in cartilage, an organ, a smooth muscle fiber, and/or a tissue, before it clears. Preferably, the compound resides in the cartilage, an organ, a smooth muscle fiber, and/or a tissue for about 1 hour to about 72 hours, preferably about 1 hour to about 42 hours, more preferably about 1 hour to about 24 hours, and most preferably about 5 hours to about 15 hours.

In an embodiment of the method of imaging of the present invention, the compound distributes to cartilage rapidly, within about 1 minute to about 1 hour after administration, and also clears fairly rapidly, within about 1 hour to about 100 hours. In some aspects of the invention, the compound distributes to and localizes in the cartilage, organ, smooth muscle fiber, and/or tissue at a concentration of about 10 micromolar to about 100 millimolar. Preferably, the compound distributes to and localizes in the cartilage at a concentration of about 10 micromolar to about 100 millimolar.

The method of imaging may further comprise detecting an inflamed cartilage and an inflamed joint in the image, because the compound localizes in the epiphyseal growth plates in the knee and shoulder joints. In an embodiment thereof, the method detects early stages of inflamed cartilage.

Another method of imaging comprises: administering to a subject in need thereof a therapeutically effective amount of an imaging agent, wherein the imaging agent is a compound of formulae I, II, III, IV, V, VI, VII, VIII, IX, X, XI, or XII, or a pharmaceutically acceptable salt thereof; and obtaining an image. The imaging agent may be used in radiography or magnetic resonance imaging, and preferably in chemical shift imaging.

In one embodiment, the labeled compound of any one of formulae I, II, III, IV, V, VI, VII, VIII, IX, X, XI, or XII is administered as the imaging agent in the method of imaging. Optionally, in that method of imaging, no unlabeled compound of any one of formulae I, II, III, IV, V, VI, VII, VIII, IX, X, XI, or XII is also administered. In another embodiment, the unlabeled compound of any one of formulae I, II, III, IV, V, VI, VII, VIII, IX, X, XI, or XII is administered as the imaging agent in the method of imaging. Optionally, in that method of imaging, no labeled compound of any one of formulae I, II, III, IV, V, VI, VII, VIII, IX, X, XI, or XII is also administered. In yet another embodiment, both the labeled compound and the unlabeled compound of any one of formulae I, II, III, IV, V, VI, VII, VIII, IX, X, XI, or XII are administered as the imaging agent in the method of imaging.

"An imaging agent" and "a contrast agent" are used interchangeably herein to refer to a chemical designed to improve the visibility of internal body structures in imaging technology, such as radiography and MRI. The most commonly used compounds for contrast enhancement are gadolinium-based. MRI contrast agents alter the relaxation times of atoms within body tissues where they are present after oral or intravenous administration. In MRI, sections of the body are exposed to a very strong magnetic field, then a radiofrequency pulse is applied causing some atoms (including those in contrast agents) to spin and then relax after the pulse stops. This relaxation emits energy which is detected by the scanner and is mathematically converted into an image.

Imaging agents may be administered by injection into the blood stream or orally, depending on the subject of interest. Oral administration is well suited to G.I. tract scans, while intravascular administration proves more useful for most other scans.

In some aspects of the invention, the method of imaging further comprises administering at least one additional therapeutic agent. In one embodiment, the at least one additional therapeutic agent is dexamethasone, any imaging agent known for use in the art, and any combination thereof. In another embodiment, the at least one additional therapeutic agent is dexamethasone.

Another embodiment of the present invention is directed to a method of diagnosing a cartilage disorder or cartilage disease comprising: administering to a subject in need thereof a therapeutically effective amount of a compound of formula I, II, III, IV, V, VI, VII, VIII, IX, X, XI, or XII, or pharmaceutically acceptable salt thereof; obtaining an image of the subject; and diagnosing a cartilage disorder or cartilage disease from the image. Preferably, the cartilage disorder may be arthritis or osteoarthritis. In a certain embodiment thereof, the method of diagnosing a cartilage disorder or cartilage disease further comprises detecting early stages of inflammation of cartilage from the image.

In one embodiment, the labeled compound of any one of formulae I, II, III, IV, V, VI, VII, VIII, IX, X, XI, or XII is administered in the method of diagnosing a cartilage disorder or cartilage disease. Optionally, in that method of diagnosing a cartilage disorder or cartilage disease, no unlabeled compound of any one of formulae I, II, III, IV, V, VI, VII, VIII, IX, X, XI, or XII is also administered. In another embodiment, the unlabeled compound of any one of formulae I, II, III, IV, V, VI, VII, VIII, IX, X, XI, or XII is administered in the method of diagnosing a cartilage disorder or cartilage disease. Optionally, in that method of diagnosing a cartilage disorder or cartilage disease, no labeled compound of any one of formulae I, II, III, IV, V, VI, VII, VIII, IX, X, XI, or XII is also administered. In yet another embodiment, both the labeled compound and the unlabeled compound of any one of formulae I, II, III, IV, V, VI, VII, VIII, IX, X, XI, or XII are administered in the method of diagnosing a cartilage disorder or cartilage disease.

Another embodiment is a method of diagnosing a cartilage disorder or cartilage disease comprising: administering to a subject in need thereof a therapeutically effective amount of a compound or a pharmaceutically acceptable salt thereof selected from the group consisting of:

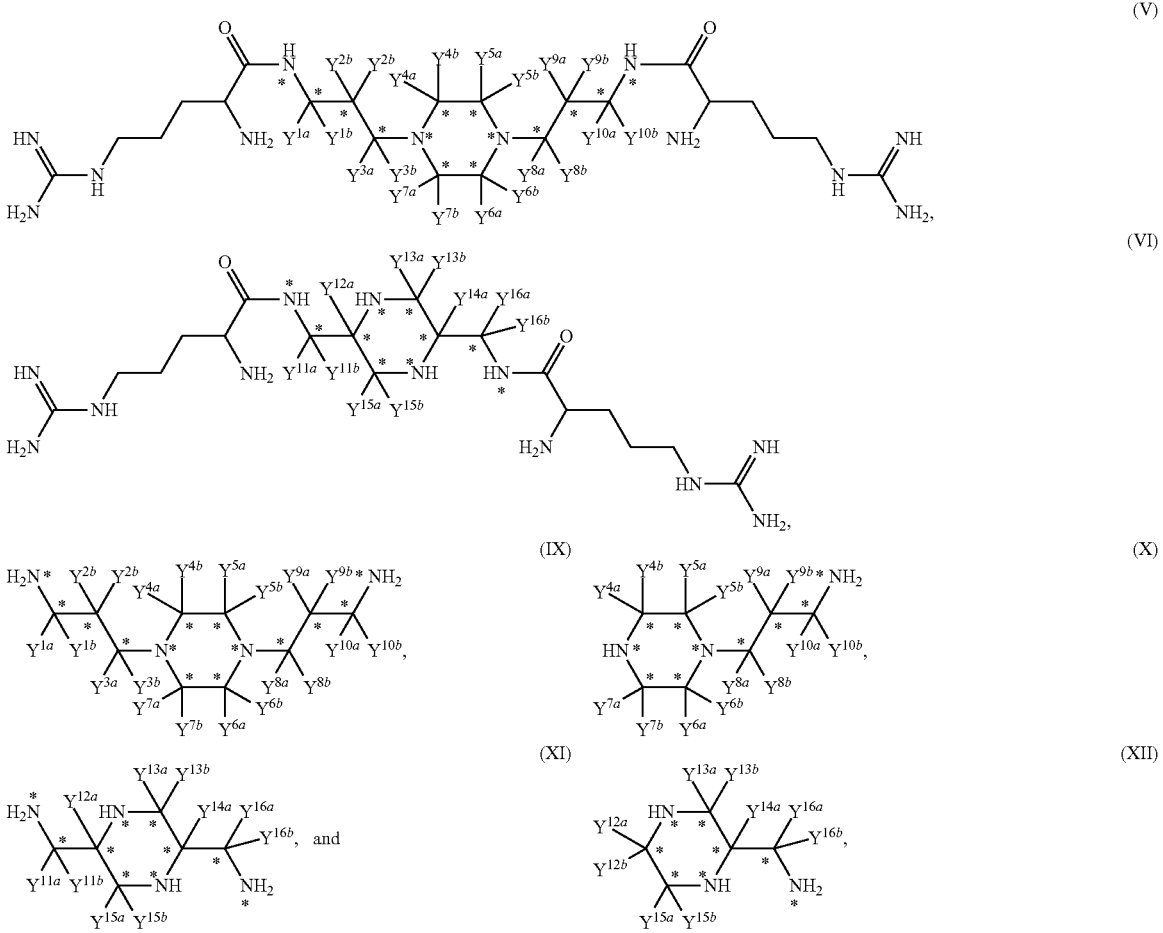

wherein:
each Y is independently selected from hydrogen, deuterium or tritium;
each carbon denoted with an asterisk is independently selected from $^{12}C$, $^{13}C$ and $^{14}C$; and
each nitrogen denoted with an asterisk is independently selected from $^{14}N$ and $^{15}N$;
obtaining an image of the subject; and
diagnosing a cartilage disorder or cartilage disease from the image.

In one embodiment, the labeled compound of any one of formulae V, VI, VII, VIII, IX, X, XI, or XII is administered in the method of diagnosing a cartilage disorder or cartilage disease. Optionally, in that method of diagnosing a cartilage disorder or cartilage disease, no unlabeled compound of any one of formulae V, VI, VII, VIII, IX, X, XI, or XII is also administered. In another embodiment, the unlabeled compound of any one of formulae V, VI, VII, VIII, IX, X, XI, or XII is administered in the method of diagnosing a cartilage disorder or cartilage disease. Optionally, in that method of diagnosing a cartilage disorder or cartilage disease, no labeled compound of any one of formulae V, VI, VII, VIII, IX, X, XI, or XII is also administered. In yet another embodiment, both the labeled compound and the unlabeled compound of any one of formulae V, VI, VII, VIII, IX, X, XI, or XII are administered in the method of diagnosing a cartilage disorder or cartilage disease.

Preferably, the method of diagnosing a cartilage disorder or cartilage disease may comprise administering a compound of formulae V, VI or IX, or a pharmaceutically acceptable salt thereof. In one embodiment, the labeled compound of formulae V, VI or IX is administered in a method of diagnosing a cartilage disorder or cartilage disease. Optionally, in that method of diagnosing a cartilage disorder or cartilage disease, no unlabeled compound of formulae V, VI or IX is also administered. In another embodiment, the unlabeled compound of formulae V, VI or IX is administered in a method of diagnosing a cartilage disorder or cartilage disease. Optionally, in that method of diagnosing a cartilage disorder or cartilage disease, no labeled compound of formulae V, VI or IX is also administered. In yet another embodiment, both the labeled compound and the unlabeled compound of formulae V, VI or IX are administered in a method of diagnosing a cartilage disorder or cartilage disease.

In a certain embodiment thereof, the method of diagnosing a cartilage disorder or cartilage disease comprises administering a compound of formula V, or a pharmaceutically acceptable salt thereof. In one embodiment, the labeled compound of formula V is administered in a method of diagnosing a cartilage disorder or cartilage disease. Optionally, in that method of diagnosing a cartilage disorder or cartilage disease, no unlabeled compound of formula V is also administered. In another embodiment, the unlabeled compound of formula V is administered in a method of diagnosing a cartilage disorder or cartilage disease. Optionally, in that method of diagnosing a cartilage disorder or cartilage disease, no labeled compound of formula V is also administered. In yet another embodiment, both the labeled compound and the unlabeled compound of formula V are administered in a method of diagnosing a cartilage disorder or cartilage disease.

The method of diagnosing a cartilage disorder or cartilage disease may comprise administering a compound of formula VI, or a pharmaceutically acceptable salt thereof. In one embodiment, the labeled compound of formula VI is administered in a method of diagnosing a cartilage disorder or cartilage disease. Optionally, in that method of diagnosing a cartilage disorder or cartilage disease, no unlabeled compound of formula VI is also administered. In another embodiment, the unlabeled compound of formula VI is administered in a method of diagnosing a cartilage disorder or cartilage disease. Optionally, in that method of diagnosing a cartilage disorder or cartilage disease, no labeled compound of formula VI is also administered. In yet another embodiment, both the labeled compound and the unlabeled compound of formula VI are administered in a method of diagnosing a cartilage disorder or cartilage disease.

In another embodiment, the method of diagnosing a cartilage disorder or cartilage disease comprises administering a compound of formula IX, or a pharmaceutically acceptable salt thereof. In one embodiment, the labeled compound of formula IX is administered in a method of diagnosing a cartilage disorder or cartilage disease. Optionally, in that method of diagnosing a cartilage disorder or cartilage disease, no unlabeled compound of formula IX is also administered. In another embodiment, the unlabeled compound of formula IX is administered in a method of diagnosing a cartilage disorder or cartilage disease. Optionally, in that method of diagnosing a cartilage disorder or cartilage disease, no labeled compound of formula IX is also administered. In yet another embodiment, both the labeled compound and the unlabeled compound of formula IX are administered in a method of diagnosing a cartilage disorder or cartilage disease.

The terms detecting, or detection, and diagnosing, or diagnosis, are readily understood by one of ordinary skill in the art.

A further embodiment of the invention is directed to a method of monitoring cartilage health comprising: administering to a subject in need thereof a therapeutically effective amount of a compound of formula I, II, III, IV, V, VI, VII, VIII, IX, X, XI, or XII, or pharmaceutically acceptable salt thereof; obtaining an image of a cartilage in the subject; and quantifying the amount of the compound in the cartilage. Cartilage health may be monitored by quantifying the amount of the compound in the cartilage, preferably, hyaline cartilage, as a proxy for proteoglycan and/or glycosaminoglycan content. The amount of imaging agent, for example, DAP, is quantified by measuring the signal strength of the protons at the resonance frequency of at least one proton on the imaging agent. In some embodiments, a background image of the protons of the resonance frequency range of interest can be subtracted from the image acquired in the presence of the imaging agent to obtain a greater signal to noise ratio. In some embodiments, chemically equivalent hydrogens, such as those present on the carbons of the piperazine ring in DAP or a metabolite thereof, are chosen to increase signal to noise ratio. Since the compound binds proportionally to the proteoglycan and/or glycosaminoglycan content of cartilage, the signal generated by the residence of the compound in the cartilage is proportional to the proteoglycan and/or glycosaminoglycan content.

In one embodiment, the labeled compound of any one of formulae I, II, III, IV, V, VI, VII, VIII, IX, X, XI, or XII is administered in the method of monitoring cartilage health. Optionally, in that method of monitoring cartilage health, no unlabeled compound of any one of formulae I, II, III, IV, V, VI, VII, VIII, IX, X, XI, or XII is also administered. In another embodiment, the unlabeled compound of any one of formulae I, II, III, IV, V, VI, VII, VIII, IX, X, XI, or XII is administered in the method of monitoring cartilage health. Optionally, in that method of monitoring cartilage health, no labeled compound of any one of formulae I, II, III, IV, V, VI, VII, VIII, IX, X, XI, or XII is also administered. In yet another embodiment, both the labeled compound and the unlabeled compound of any one of formulae I, II, III, IV, V, VI, VII, VIII, IX, X, XI, or XII are administered in the method of monitoring cartilage health.

Another embodiment is a method of monitoring cartilage health comprising: administering to a subject in need thereof a therapeutically effective amount of a compound or a pharmaceutically acceptable salt thereof selected from the group consisting of:

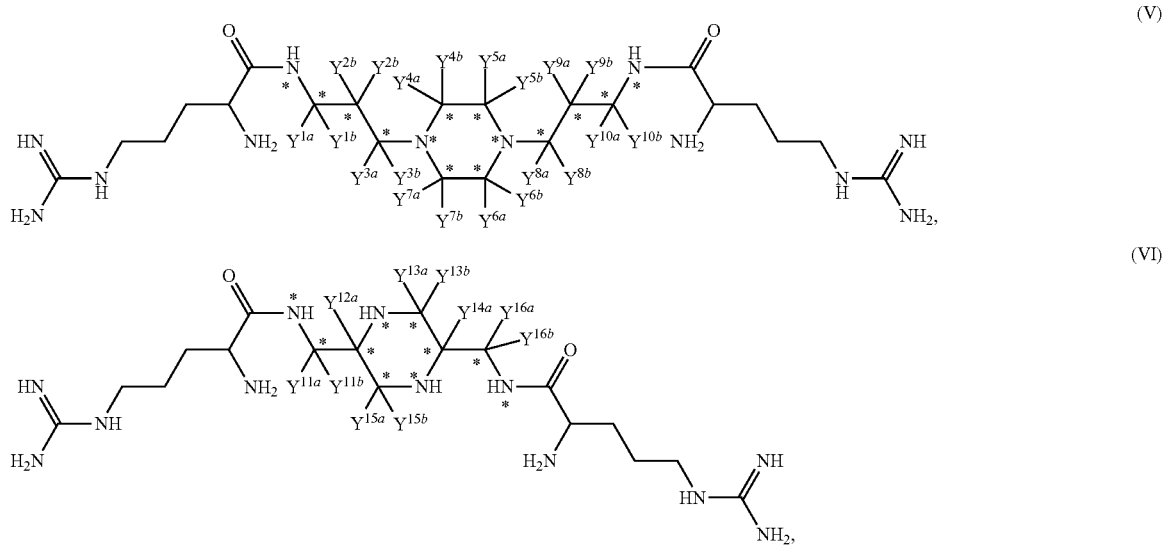

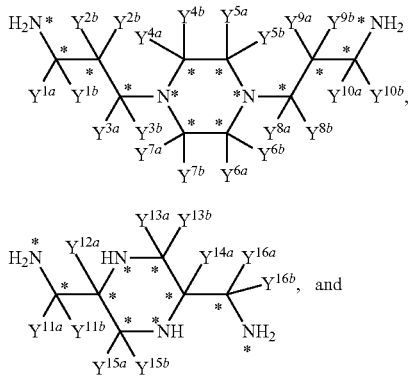
(IX)

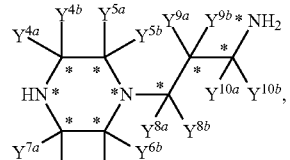
(X)

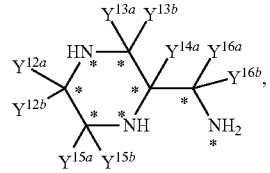
(XI)

(XII)

wherein:
each Y is independently selected from hydrogen, deuterium or tritium;
each carbon denoted with an asterisk is independently selected from $^{12}C$, $^{13}C$ and $^{14}C$; and
each nitrogen denoted with an asterisk is independently selected from $^{14}N$ and $^{15}N$;
obtaining an image of a cartilage in the subject; and
quantifying the amount of the compound in the cartilage.

In one embodiment, the labeled compound of any one of formulae V, VI, VII, VIII, IX, X, XI, or XII is administered in the method of monitoring cartilage health. Optionally, in that method of monitoring cartilage health, no unlabeled compound of any one of formulae V, VI, VII, VIII, IX, X, XI, or XII is also administered. In another embodiment, the unlabeled compound of any one of formulae V, VI, VII, VIII, IX, X, XI, or XII is administered in the method of monitoring cartilage health. Optionally, in that method of monitoring cartilage health, no labeled compound of any one of formulae V, VI, VII, VIII, IX, X, XI, or XII is also administered. In yet another embodiment, both the labeled compound and the unlabeled compound of any one of formulae V, VI, VII, VIII, IX, X, XI, or XII are administered in the method of monitoring cartilage health.

Preferably, the method of monitoring cartilage health may comprise administering a compound of formulae V, VI or IX, or a pharmaceutically acceptable salt thereof. In one embodiment, the labeled compound of formulae V, VI or IX is administered in a method of monitoring cartilage health. Optionally, in that method of monitoring cartilage health, no unlabeled compound of formulae V, VI or IX is also administered. In another embodiment, the unlabeled compound of formulae V, VI or IX is administered in a method of monitoring cartilage health. Optionally, in that method of monitoring cartilage health, no labeled compound of formulae V, VI or IX is also administered. In yet another embodiment, both the labeled compound and the unlabeled compound of formulae V, VI or IX are administered in a method of monitoring cartilage health.

In a certain embodiment thereof, the method of monitoring cartilage health comprises administering a compound of formula V, or a pharmaceutically acceptable salt thereof. In one embodiment, the labeled compound of formula V is administered in a method of monitoring cartilage health. Optionally, in that method of monitoring cartilage health, no unlabeled compound of formula V is also administered. In another embodiment, the unlabeled compound of formula V is administered in a method of monitoring cartilage health. Optionally, in that method of monitoring cartilage health, no labeled compound of formula V is also administered. In yet another embodiment, both the labeled compound and the unlabeled compound of formula V are administered in a method of monitoring cartilage health.

The method of monitoring cartilage health may comprise administering a compound of formula VI, or a pharmaceutically acceptable salt thereof. In one embodiment, the labeled compound of formula VI is administered in a method of monitoring cartilage health. Optionally, in that method of monitoring cartilage health, no unlabeled compound of formula VI is also administered. In another embodiment, the unlabeled compound of formula VI is administered in a method of monitoring cartilage health. Optionally, in that method of monitoring cartilage health, no labeled compound of formula VI is also administered. In yet another embodiment, both the labeled compound and the unlabeled compound of formula VI are administered in a method of monitoring cartilage health.

In another embodiment, the method of monitoring cartilage health comprises administering a compound of formula IX, or a pharmaceutically acceptable salt thereof. In one embodiment, the labeled compound of formula IX is administered in a method of monitoring cartilage health. Optionally, in that method of monitoring cartilage health, no unlabeled compound of formula IX is also administered. In another embodiment, the unlabeled compound of formula IX is administered in a method of monitoring cartilage health. Optionally, in that method of monitoring cartilage health, no labeled compound of formula IX is also administered. In yet another embodiment, both the labeled compound and the unlabeled compound of formula IX are administered in a method of monitoring cartilage health.

III. Labeled Compounds

Novel labeled compounds are disclosed, as well as pharmaceutically acceptable salts thereof and methods of use.

An embodiment of the invention is a labeled compound of the formula (I), as described above, or a pharmaceutically acceptable salt thereof:

Y-M-X-L-A-L'-X'-M'-Y'  (I)

wherein:
A is a substituted or unsubstituted aromatic or non-aromatic, carbocyclic or heterocyclic ring or a linear moiety;
L and L' are the same or different and are linkers;
X and X' are the same or different and are absent or are a functional group that attaches the linker L to M and the linker L' to M', respectively;

M and M' are the same or different and are absent or is a linker that attaches X to Y and X' to Y', respectively; and Y and Y' are the same or different and are a moiety containing one or more cationic atoms or groups or one or more groups that become cationic under physiological conditions.

The terms used above in discussing other embodiments of the invention, such as labeled, imaging, cartilage, organ, smooth muscle fiber and tissue, have the same meaning in this embodiment as they have in the other embodiments.

In another embodiment of the invention, the labeled compound is represented by the formula II or a pharmaceutically acceptable salt thereof:

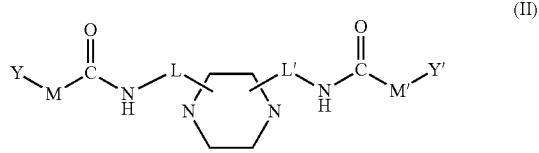
(II)

wherein each of L, L', M, M', Y and Y' are as previously described.

In another embodiment of the invention, the labeled compound is represented by the formula III or a pharmaceutically acceptable salt thereof:

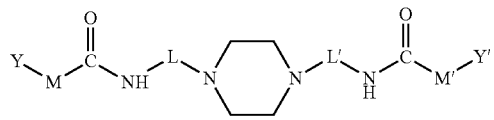
(III)

wherein L, L', M, M', Y and Y' are as previously described.

In yet another embodiment of the invention, the labeled compound is represented by the formula IV or a pharmaceutically acceptable salt thereof:

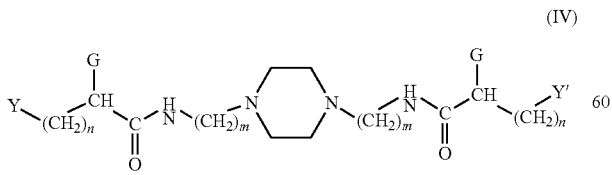
(IV)

wherein Y and Y' are as previously described and n is 3 to 5, m is 3 to 6 and G is selected from —NH$_2$ and OH. Most preferably, G is amino.

Yet another embodiment of the invention, the labeled compound is represented by any of formula II, III or IV and Y and Y' are independently selected from the group consisting of

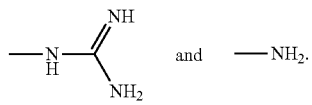

Most preferably G is —NH$_2$ and Y and Y' are

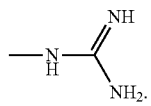

In an embodiment, the labeling of the compound of formulae II, III or IV is in the central moiety, and preferably, in the piperazine.

In one embodiment, the labeled compound is DAP, depicted below as formula V, or a pharmaceutically acceptable salt or metabolite thereof:

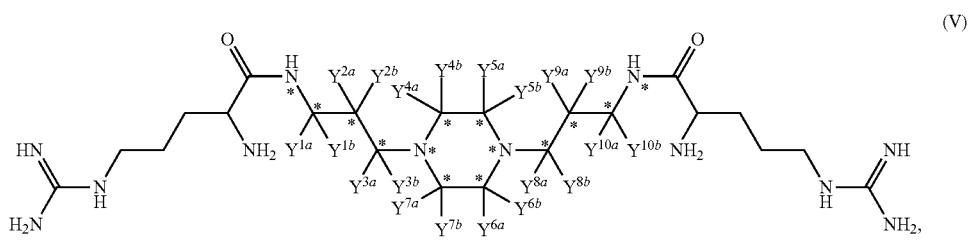
(V)

e.g., labeled 2-Amino-5-guanidino-pentanoic acid (3-{4-[3-(2-amino-5-guanidino-pentanoylamino)-propyl]-piperazin-1-yl}-propyl)-amide, wherein:

each Y is independently selected from hydrogen, deuterium or tritium;

each carbon denoted with an asterisk is independently selected from $^{12}C$, $^{13}C$ and $^{14}C$; and each nitrogen denoted with an asterisk is independently selected from $^{14}N$ and $^{15}N$, and wherein at least one Y is deuterium or tritium, one carbon is $^{13}C$ or $^{14}C$, or one nitrogen is $^{15}N$.

In another embodiment, the labeled compound is formula VII, a stereoisomer of formula V, as depicted below:

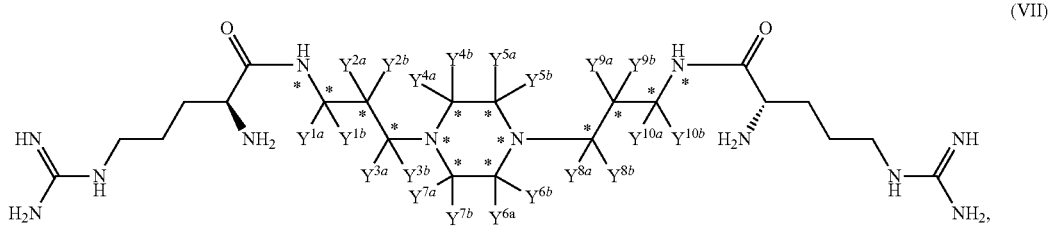

(VII)

or a pharmaceutically acceptable salt thereof, wherein:
each Y is independently selected from hydrogen, deuterium or tritium;
each carbon denoted with an asterisk is independently selected from $^{12}C$, $^{13}C$ and $^{14}C$; and
each nitrogen denoted with an asterisk is independently selected from $^{14}N$ and $^{15}N$, and
wherein at least one Y is deuterium or tritium, one carbon is $^{13}C$ or $^{14}C$, or one nitrogen is $^{15}N$.

In an embodiment, the compound is formula IX, a metabolite of formula V, as depicted below:

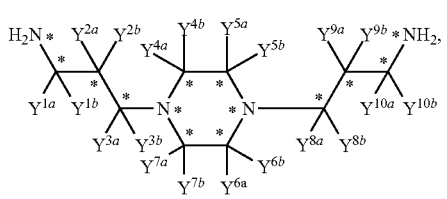

(IX)

or a pharmaceutically acceptable salt thereof, wherein:
each Y is independently selected from hydrogen, deuterium or tritium;
each carbon denoted with an asterisk is independently selected from $^{12}C$, $^{13}C$ and $^{14}C$; and
each nitrogen denoted with an asterisk is independently selected from $^{14}N$ and $^{15}N$. In one embodiment, the compound of formula IX is labeled. In another embodiment, the compound of formula IX is unlabeled.

In another embodiment, the compound is formula X, a metabolite of formula V, as depicted below:

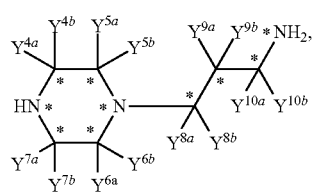

(X)

or a pharmaceutically acceptable salt thereof, wherein:
each Y is independently selected from hydrogen, deuterium or tritium;
each carbon denoted with an asterisk is independently selected from $^{12}C$, $^{13}C$ and $^{14}C$; and
each nitrogen denoted with an asterisk is independently selected from $^{14}N$ and $^{15}N$. In one embodiment, the compound of formula X is labeled. In another embodiment, the compound of formula X is unlabeled.

In another embodiment, the labeled compound of the invention is a compound related to DAP, depicted as formula VI below, or a pharmaceutically acceptable salt or metabolite thereof:

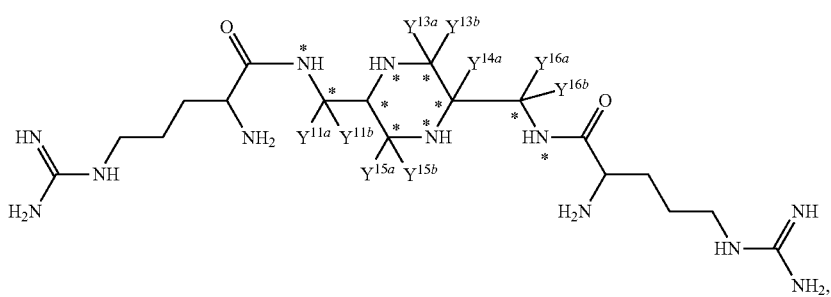

(VI)

e.g., 2-Amino-5-guanidino-pentanoic acid {5-[(2-amino-5-guanidino-pentanoylamino)-methyl]-piperazin-2-ylmethyl}-amide, wherein:
each Y is independently selected from hydrogen, deuterium or tritium;
each carbon denoted with an asterisk is independently selected from $^{12}C$, $^{13}C$ and $^{14}C$; and
each nitrogen denoted with an asterisk is independently selected from $^{14}N$ and $^{15}N$, and
wherein at least one Y is deuterium or tritium, one carbon is $^{13}C$ or $^{14}C$, or one nitrogen is $^{15}N$.

In a certain embodiment, the labeled compound is formula VIII, a stereoisomer of formula VI, as depicted below:

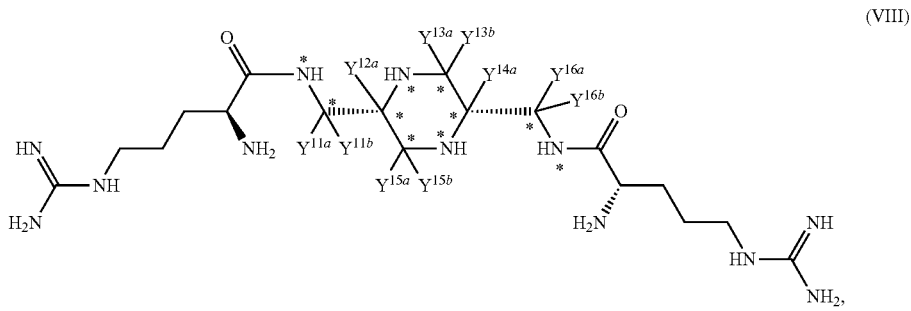

(VIII)

or a pharmaceutically acceptable salt thereof, wherein:

each Y is independently selected from hydrogen, deuterium or tritium;

each carbon denoted with an asterisk is independently selected from $^{12}C$, $^{13}C$ and $^{14}C$; and each nitrogen denoted with an asterisk is independently selected from $^{14}N$ and $^{15}N$, and wherein at least one Y is deuterium or tritium, one carbon is $^{13}C$ or $^{14}C$, or one nitrogen is $^{15}N$.

In a further embodiment, the compound is formula XI, a metabolite of formula VI, as depicted below:

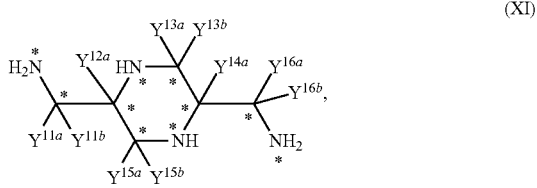

(XI)

or a pharmaceutically acceptable salt thereof, wherein:

each Y is independently selected from hydrogen, deuterium or tritium;

each carbon denoted with an asterisk is independently selected from $^{12}C$, $^{13}C$ and $^{14}C$; and each nitrogen denoted with an asterisk is independently selected from $^{14}N$ and $^{15}N$. In one embodiment, the compound of formula XI is labeled. In another embodiment, the compound of formula XI is unlabeled.

In a further embodiment of the invention, the compound is formula XII, a metabolite of formula VI, as depicted below:

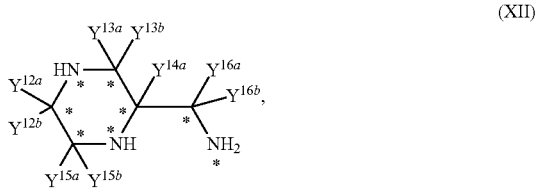

(XII)

or a pharmaceutically acceptable salt thereof, wherein:

each Y is independently selected from hydrogen, deuterium or tritium;

each carbon denoted with an asterisk is independently selected from $^{12}C$, $^{13}C$ and $^{14}C$; and each nitrogen denoted with an asterisk is independently selected from $^{14}N$ and $^{15}N$. In one embodiment, the compound of formula XII is labeled. In another embodiment, the compound of formula XII is unlabeled.

The labeled compound of formulae I, II, III, IV, V, VI, VII, or VIII, and the labeled or unlabeled compound of formulae IX, X, XI, or XII may be used as an imaging agent and may be administered to a subject for imaging cartilage, an organ, a smooth muscle fiber, and/or a tissue.

The labeled compound of formulae I, II, III, IV, V, VI, VII, or VIII, and the labeled or unlabeled compound of formulae IX, X, XI, or XII may also be used for imaging and detecting growth disorders (e.g., achondroplasia) or for urograms to detect non-stone defects in the kidney, bladder, ureters, as well as to avoid cystograms, where one could likely quantitate residual volumes, etc. Further, the compound may be used for imaging and detecting inflamed cartilage and inflamed joints, because it localizes the epiphyseal growth plates in the knee and shoulder joints. In a preferred embodiment thereof, the compound may be used for detecting early stages of inflamed cartilage.

In some embodiments of the invention, one or both arginines of the compounds of formulae V and VI (or the compounds of formulae VII and VIII) are substituted by one or more positively charged amino acids, their derivatives, or similarly charged compounds, e.g., lysine, histidine, ornithine. The arginines in the compounds of formulae V and VI (or the compounds of formulae VII and VIII) or positively charged amino acids substituted for such arginines can be naturally occurring amino acids (i.e., L-amino acids), their enantiomers (i.e., D-amino acids), or racemic or other mixtures thereof "Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes D and L or (+) and (−) are employed to designate the sign of rotation of plane-polarized light by the compound, with (−) or L meaning that the compound is levorotatory. A compound prefixed with (+) or D is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

In other embodiments of the invention, the compounds disclosed herein contain at least one cyclic hydrophobic moiety, e.g., one or a combination of aliphatic and aromatic rings including fused rings. Compounds of interest contain at least one cyclic hydrophobic moiety and at least two positively charged or partially charged moieties at physiological pH.

Special consideration should be given to the design of peptide-based therapeutic agents, since such agents may cause unwanted and often severe immunological reactions once administered to a subject. The compounds of the invention are designed to be of sufficiently low molecular weight to minimize immunogenicity issues. In one embodiment, in order to avoid activation of the immune response, the compound is designed such that its molecular weight is less than about 5000 daltons, such as less than or about 1000 daltons, e.g., about 500 daltons. In one embodiment, the molecular weight of the compound is about 512 daltons.

It is preferable that the compounds disclosed herein do not bind, or otherwise interfere with the function of the ERG, a potassium ion channel that contributes to the electrical conductivity of the heart. Inhibition of this potassium channel may lead to potentially fatal long QT syndrome, and some otherwise successful drug candidates have exhibited human ERG binding.

In addition, it is preferable that the compounds disclosed herein do not inhibit or serve as substrates for membrane-bound cytochrome p450 (CYP) enzymes. CYPs are major enzymes involved in drug metabolism, and modulation of CYP activity may interfere with clearance and metabolism of other drugs administered to a subject, causing unwanted drug interactions.

Also preferably, the compounds disclosed herein do not exhibit significant plasma protein binding in vitro (e.g., albumin binding). Because the compounds of the invention are largely unbound to plasma proteins, they exhibit short activity half-lives minimizing the risk of accumulation-based overdose.

III. Synthesis of Labeled Compounds

The labeled compounds and their pharmaceutically acceptable salts and metabolites described herein are prepared using a variety of methods starting from commercially available compounds, known compounds, or compounds prepared by known methods. Exemplary synthetic routes to one of the compounds described herein are included in the schemes below. The schemes below are also applicable to the stereoisomer compound of formula VI by selecting the appropriate stereoisomeric starting compounds. Other compounds of the invention may be synthesized following a similar synthetic scheme. It is understood by those skilled in the art that the order of steps shown herein may be changed to accommodate functionality in the target molecule. It is also understood by those skilled in the art that various protection and deprotection steps may be required for synthesis. The need for protection and deprotection, and the selection of appropriate protecting groups are found, for example, in Greene and Wuts, Protecting Groups in Organic Synthesis, Second Edition, John Wiley & Sons (1991), which is incorporated herein by reference in its entirety.

In some embodiments of the present invention, the protecting group is tertiary butyloxycarbonyl group (Boc). In other embodiments of the present invention, the protecting group is 2,2,4,6,7-Pentamethyldihydrobenzofuran-5-sulfonyl group (Pbf). In another embodiment, amino acid protecting group may be, but is not limited to, 2,2,5,7,8-pentamethyl-chroman-6-sulphonyl (PMC).

Protecting groups may be removed by a variety of routes. Removal of protecting group comprises, e.g., treating protected compound with trifluoroacetic acid (TFA), aqueous HCl, or heating in acetic acid. Because removal of protecting groups, e.g., removal of protecting groups under acidic conditions, can result in production of cationic species that can alkylate the functional groups on the peptide chain, scavengers may be added during the deprotection step to react with any of the free reactive species. Examples of scavengers include, but are not limited to, water, anisol derivatives and thiol derivatives. Thus, in one embodiment, removal of protecting groups comprises treating protected compound with TFA and a scavenger (e.g., TFA and water).

Various solvents, e.g., organic solvents, may be used in the steps of the synthesis. Appropriate solvents include, but are not limited to, dimethyl sulfoxide, dimethylformamide (DMF), tetrahydrofuran, methanol, ethanol, methylene chloride, toluene, and acetone. In some embodiments, the solvent is DMF.

Suitable acid binding agents may be used in the steps of the synthesis. These include, but are not limited to, organic bases, such as, for example, pyridine, triethylamine, triethanolamine, 1,8-diazabicyclo[5.4.0]undec-7-ene (DBU), and diisopropylethylamine (DIEA); and inorganic bases, such as, for example, sodium hydride, potassium carbonate, and sodium carbonates. In some embodiments, the acid binding agent is DIEA.

Synthesis may include peptide coupling reagents. Peptide coupling reagents may include, but are not limited to, 1-ethyl-3-(3-dimethylaminopropyl) carbodiimide (EDC), N-Hydroxybenzotriazole (HOBO, carbonyldiimidazole (CDI), dicyclohexylcarbodiimide (DCC), active N-hydroxy-succinamide (OSu) ester, O-Benzotriazole-N,N,N',N'-tetramethyl-uronium-hexafluoro-phosphate (HBTU), and combinations thereof. In one embodiment, the peptide coupling reagent is HBTU. In another embodiment, the peptide coupling reagent is EDC/HOBt. In yet another embodiment, the peptide coupling reagent is an active OSu ester.

Additionally, the synthesis may include a step in which a crude product is purified, e.g., by column chromatography. The desired products of each step or series of steps may be separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

In one scheme, the following embodiment of the labeled compound of formula VII was synthesized, depicted as formula XIII:
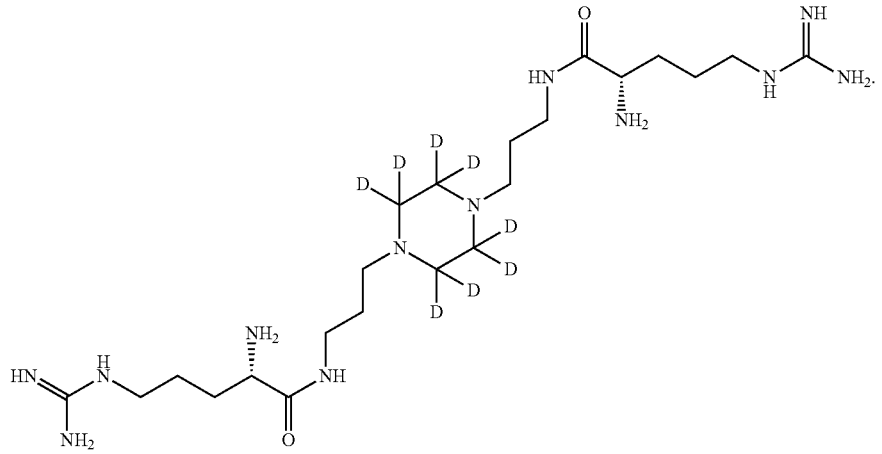
This compound was synthesized according to the following reaction scheme:
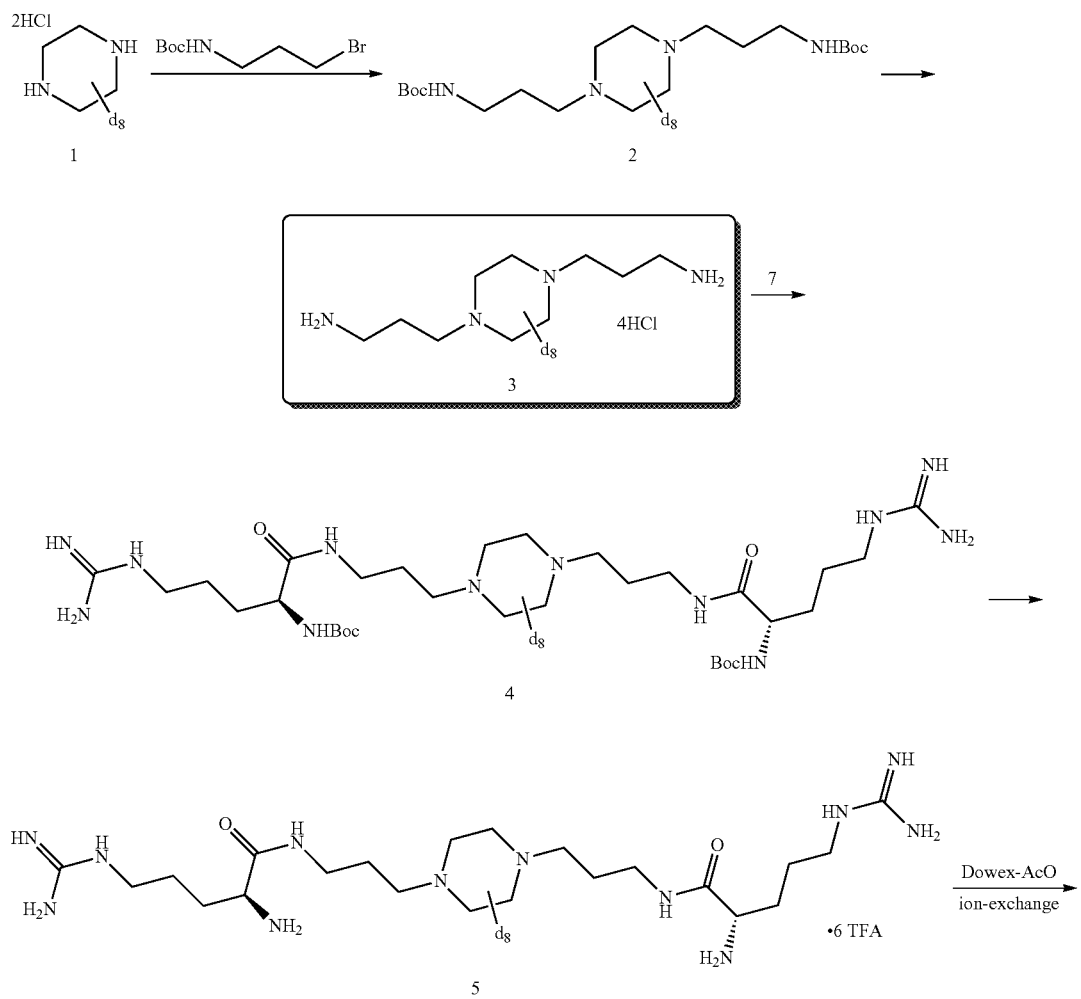

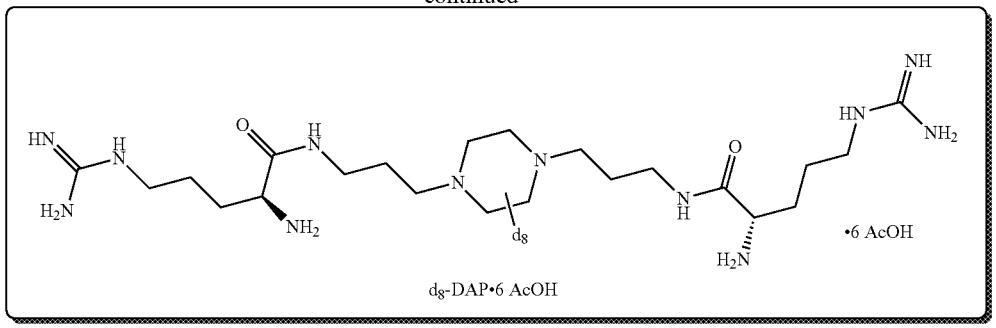

d₈-DAP•6 AcOH

The first step in synthesis of formula XIII is the synthesis of $d_8$-BAP (3). This compound may be synthesized by starting with bromide and compound. Alkylation proceeds in good yield and compound 2 can be purified by normal phase chromatography, if desired.

The next step is Boc deprotection. The protecting groups of compound 2 may be removed by any method known in the art in order to obtain compound 3. Deprotection can be achieved by, e.g., removal of protecting groups using trifluoroacetic acid (TFA) and water, TFA and water or another scavenger, including, but not limited to aqueous HCl, or heating in acetic acid.

Coupling and purification by HPLC gave the bis-Boc $d_8$-DAP (4). Deprotection followed by extensive HPLC resulted in purified compound 5.

IV. Pharmaceutical Compositions

Another embodiment of the invention is directed to a pharmaceutical composition comprising a labeled compound of any of formulae I, II, III, IV, V, VI, VII, and VIII, and a pharmaceutically acceptable carrier. Yet another embodiment of the invention is directed to a pharmaceutical composition comprising a compound of any of formulae IX, X, XI and XII, and a pharmaceutically acceptable carrier, wherein the compound may be labeled or unlabeled. In one embodiment thereof, the pharmaceutical composition comprises the labeled compound of formulae IX, X, XI or XII. Optionally, that pharmaceutical composition may contain the labeled compound of formulae IX, X, XI or XII and no unlabeled compound of that formula. In another embodiment, the pharmaceutical composition comprises the unlabeled compound of formulae IX, X, XI or XII. Optionally, that pharmaceutical composition may contain the unlabeled compound of formulae IX, X, XI or XII and no labeled compound of that formula. In yet another embodiment, the pharmaceutical composition comprises both the labeled compound and the unlabeled compound of formulae IX, X, XI or XII.

The terms used above in discussing other embodiments of the invention, such as labeled, imaging, cartilage, organ, smooth muscle fiber and tissue, have the same meaning in this embodiment as they have in the other embodiments.

The pharmaceutical composition may contain, in addition to a compound of the invention, a pharmaceutically acceptable carrier or excipient. The term "pharmaceutically acceptable" means a nontoxic material that is compatible with the physical and chemical characteristics of the active ingredient and does not interfere with the effectiveness of the biological activity of the active. The compositions may contain various diluents, fillers, salts, buffers, stabilizers, solubilizers, and other materials well known in the art. The characteristics of the carrier will depend on the route of administration, and are generally well known in the art.

The pharmaceutical composition may be adapted for enteral administration—administration of the composition, wherein the composition is absorbed through the digestive tract, e.g., oral ingestion, rectal administration. In other embodiments, the pharmaceutical composition of the invention may be adapted for parenteral administration—administration of the composition, wherein the composition is introduced via a route other than digestive tract, e.g., intravenous, intra-articular, subcutaneous, cutaneous, nasal, pulmonary, vaginal, buccal route. In a preferred embodiment, the pharmaceutical composition of the invention may be adapted for oral or intravenous administration.

The pharmaceutical composition may be in the solid or the liquid dosage form. The solid dosage form and liquid dosage form may be suitable for administration to a patient on an as needed basis, such as, for example in methods of imaging and diagnosing cartilage disorders and diseases and for monitoring cartilage health.

Suitable pharmaceutical compositions, e.g., compositions for oral administration, may be prepared as described in references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", $6^{th}$ Edition, Ansel et. al., (Media, Pa.: Williams and Wilkins, 1995), incorporated herein by reference, which provide information on carriers, materials (e.g., coating materials), equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit® (Roth Pharma, Westerstadt, Germany), Zein, shellac, and polysaccharides. Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants.

Diluents, also termed "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powder sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

The pharmaceutical composition of the invention may be designed to provide delayed, sustained, pulsatile or other modified release.

If desired, the tablets, beads, granules or particles may also contain a minor amount of nontoxic auxiliary substances such as wetting or emulsifying agents, dyes, pH buffering agents, and preservatives.

Bioadhesive formulations may also be utilized to enhance uptake or modify release. Such formulations are known in the art. See, for example, U.S. Patent Application Publication No. 2006/0045865 to Jacob, the contents of which are incorporated herein by reference.

The compounds of the invention can be administered in a pharmaceutical composition as an aqueous solution as a bolus and/or intravenous infusion, subcutaneous injection, or orally. In a preferred embodiment, the compound may be administered by intravenous injection in a carrier such as distilled sterile water, saline, buffered saline, or another pharmaceutically acceptable excipient for injection.

Pharmaceutical compositions adapted for delivery via nasal or pulmonary administration may also be useful. Aerosols for the delivery of therapeutic agents to the respiratory tract have been described, for example, Adjei, A. and Garren, *J. Pharm. Res.,* 7: 565-569 (1990); and Zanen, P. and Lamm, J.-W. J. *Int. J. Pharm.,* 114: 111-115 (1995). The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchioli which then lead to the ultimate respiratory zone, the alveoli, or deep lung. Gonda, I. "Aerosols for delivery of therapeutic and diagnostic agents to the respiratory tract," in *Critical Reviews in Therapeutic Drug Carrier Systems,* 6:273-313 (1990). The deep lung, or alveoli, is the primary target of inhaled therapeutic aerosols for systemic drug delivery.

Drugs administered by inhalation may come as liquid aerosol formulations.

For injectable compositions (e.g., intravenous compositions), the carrier is distilled sterile water, saline, buffered saline, or another pharmaceutically acceptable excipient for injection. Additives may include preservatives and acids or base to adjust pH, to alter solubility or uptake.

When the pharmaceutical composition is in a liquid dosage form, it may have a pH between about 6.5 and about 8.5. In certain embodiments, the pharmaceutical composition contains an acid, a base, and or a combination thereof, which is used to adjust the pH to the desired pH range. In a certain embodiment, the pH is from about 7.0 to about 8.0, and preferably from about 7.2 to about 7.6.

Any acid or base known for use in pharmaceutical compositions may be used in accordance with the invention. In a certain embodiment, the acid or base is selected from carbonate, bicarbonate, sodium hydroxide, acetic acid, sulfuric acid, hydrochloric acid, and any combination thereof. Preferably, hydrochloric acid may be used as the acid, and sodium hydroxide may be used as the base.

Any salt known for use in pharmaceutical compositions may be used in accordance with the invention. In a certain embodiment, the salt is selected from acetate, chloride, bromide, iodide, and any combination thereof.

In another embodiment, the pharmaceutical composition may be adjusted to about 5 mg/ml to about 500 mg/ml, preferably, to about 5 mg/ml to about 250 mg/ml, more preferably, to about 5 mg/ml to about 50 mg/ml, and most preferably, to about 10 mg/ml to about 25 mg/ml.

In a certain embodiment, the pharmaceutical composition is administered to a subject for imaging cartilage, an organ, a smooth muscle fiber, and/or a tissue, and preferably, may be for imaging the prostate, thymus, kidney, ureter and bladder. In another embodiment, the pharmaceutical composition is administered to a subject for imaging proteoglycan and glycosaminoglycan content of cartilage, wherein the cartilage may be selected from the group consisting of hyaline cartilage, fibrocartilage and elastic cartilage, and preferably, may be hyaline cartilage. In certain embodiments, the imaging may be radiography or magnetic resonance imaging.

In a further embodiment, the compound in the pharmaceutical composition localizes in cartilage, an organ, a smooth muscle fiber, and/or a tissue of the subject, and may have a residence time of about 1 hour to about 24 hours, and more preferably, about 5 hours to about 15 hours.

In an embodiment of the invention, the pharmaceutical composition is used to image the prostate, thymus, kidney, ureter and/or bladder.

In another embodiment, the pharmaceutical composition may be administered to a subject for imaging proteoglycan and glycosaminoglycan content of cartilage. In a further embodiment, the compound administered in the pharmaceutical composition to a subject for imaging localizes in cartilage, an organ, a smooth muscle fiber, and/or a tissue of the subject.

In one embodiment, the pharmaceutical composition comprises the labeled DAP compound of formula V (or its stereoisomer of formula VII), or a pharmaceutically acceptable salt thereof.

In an embodiment thereof, the composition may be adapted for parenteral administration in an injection, the compound is dissolved in water with appropriate tonicity and molality modifiers (such as phosphate buffered saline). The labeled DAP compound of formula V (or its stereoisomer of formula VII) is water-soluble at greater than 100 mg/ml. In the one embodiment, the labeled DAP compound of formula V (or its stereoisomer of formula VII) is adapted as a sterile solution for IV administration. In one aspect, the molality of the pharmaceutical composition in which the labeled DAP compound of formula V (or its stereoisomer of formula VII) is adapted for IV administration. The composition may be adjusted to about 290 mOsm/L with sodium, and the pH may be adjusted to between about 7.0 and about 7.8, preferably, about 7.4, for example, with sodium hydroxide or hydrochloric acid. Preferably the pharmaceutical composition is administered as an intravenous bolus by slow push.

In another aspect, the molality of the pharmaceutical composition in which the labeled DAP compound of formula V (or its stereoisomer of formula VI) is adapted for oral administration. The composition may be preferably isotonic with a pH adjusted to between about 7.0 and about 7.8, preferably, about 7.4.

Another embodiment is a pharmaceutical composition comprising a compound of formula IX or a pharmaceutically acceptable salt thereof. In one embodiment thereof, the pharmaceutical composition comprises the labeled compound of formula IX or a pharmaceutically acceptable salt thereof. Optionally, that pharmaceutical composition contains the labeled compound of formula IX and no unlabeled compound of that formula. In another embodiment thereof, the pharmaceutical composition comprises the unlabeled compound of formula IX or a pharmaceutically acceptable salt thereof. Optionally, that pharmaceutical composition contains the unlabeled compound of formula IX and no labeled compound of that formula. In yet another embodiment, the pharmaceutical composition contains both the labeled compound and the unlabeled compound of formula IX.

When the compound is unlabeled, each Y is hydrogen, each carbon is $^{12}C$, and each nitrogen is $^{14}N$, depicted as follows as formula IX*:

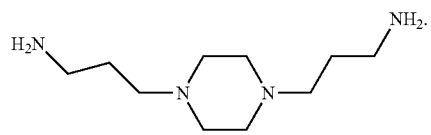 [SMILES: NCCCN1CCN(CCCN)CC1]

This unlabeled formula IX*, 1,4-Bis(3-aminopropyl)piperazine, or "BAP", is commercially available, for example, by purchase from Sigma Aldrich.

In a preferred embodiment thereof, the pharmaceutical composition of the invention may be adapted for oral or intravenous administration.

In a certain embodiment, the pharmaceutical composition is formulated for oral delivery, and may be in a liquid or a solid dosage form. In a certain embodiment, when in a liquid dosage form, the pharmaceutical composition may be in the form of a liquid gel capsule. In another embodiment, when in a solid dosage form, because pure BAP is a liquid, BAP can be compounded as a salt and formulated into the solid oral dosage form. For example, in certain embodiments, BAP may be compounded as a hydrochloride (e.g., mono- or di-) salt, or with any halogen, e.g., fluoride, chloride, bromide or iodide, or any acetate, e.g., ethyl acetate, methyl acetate, sodium acetate and the like. The solid dosage form may be any form readily understood in the art for pharmaceutical administration.

When formulated as a solid dosage form for oral administration, the amount of BAP administered may be about 100 mg to about 5 grams per dose, preferably about 300 mg to about 4.5 grams per dose, more preferably, about 600 mg to about 4 grams per dose, still more preferably, about 900 mg to about 3.5 grams per dose, and most preferably about 1 gram to about 3 grams per dose.

In an embodiment, the pharmaceutical composition formulated in a liquid dosage form, preferably for intravenous administration, contains about 1 to about 75 mg/mL of the compound of formula IX, preferably about 5 to about 70 mg/mL of the compound of formula IX, and more preferably about 10 to about 56 mg/mL of the compound of formula IX.

When the pharmaceutical composition contains 56 mg/mL of liquid BAP, the liquid pharmaceutical composition has an osmolarity of about 280 milli-osmoles per kilogram (mOsm/kg), which is within the range of normal human physiologic osmolarity. A pharmaceutical composition containing a lower concentration of BAP should preferably also contain enough of a salt (e.g., sodium chloride) necessary to bring the final osmolarity of the composition into the range of about 250 mOsm/kg to about 350 mOsm/kg, more preferably about 260 mOsm/kg to about 320 mOsm/kg, and most preferably about 260 mOsm/kg to about 300 mOsm/kg. One of ordinary skill in the art would readily understand how to accomplish the process of obtaining the desired osmolarity given the disclosure herein.

An embodiment of the pharmaceutical composition containing BAP is in liquid dosage form for intravenous administration, wherein the liquid dosage form is isotonic, pH neutral (i.e., pH between about 7.2 to about 7.6), and sterile. Preferably, the pharmaceutical composition is in liquid dosage form for intravenous administration, further comprising a salt (e.g., sodium chloride) in an amount sufficient to adjust the osmolarity to about 260 mOsm/kg to about 300 mOsm/kg, and an acid, preferably, hydrochloric, sulfuric or acetic acid, in an amount sufficient to adjust the pH to about 7.4, and the liquid dosage form is isotonic and sterile.

An isotonic composition has the same salt concentration as surrounding blood and cells. Isotonic solutions are commonly used for intravenous administration. A sterile composition is a mixture wherein all forms of life have been destroyed.

Another embodiment is directed to a method of imaging comprising administering to a subject in need thereof a therapeutically effective amount of a pharmaceutical composition comprising a compound of formula IX, or a pharmaceutically acceptable salt thereof, and a pharmaceutically acceptable carrier, as described above, and obtaining an image. In another embodiment, the method of imaging comprises administering to a subject in need thereof a therapeutically effective amount of a pharmaceutical composition comprising a compound of formula IX, or pharmaceutically acceptable salt thereof, and obtaining an image of a cartilage, an organ, a smooth muscle fiber, and/or a tissue of the subject.

In one embodiment, the pharmaceutical composition administered in a method of imaging comprises the labeled compound of formula IX. Optionally, that pharmaceutical composition contains the labeled compound of formula IX and no unlabeled compound of that formula. In another embodiment, the pharmaceutical composition administered in a method of imaging comprises the unlabeled compound of formula IX. Optionally, that pharmaceutical composition contains the unlabeled compound of formula IX and no labeled compound of that formula. In yet another embodiment, the pharmaceutical composition administered in a method of imaging comprises both the labeled compound and the unlabeled compound of formula IX.

The method of imaging may further comprise assessing osteoarthritis by tracking proteoglycan and glycosaminoglycan content of cartilage in the image. BAP non-covalently binds to heparins, which are a constituent of the proteoglycan portion of cartilage and are molecularly similar to the glycosaminoglycan portion of cartilage. As such, BAP and its pharmaceutically acceptable salts can be used to image the proteoglycan, glycosaminoglycan and mucopolysaccharide content of cartilage as a marker of cartilage health. Since BAP binds proteoglycans, glycasominoglycans, and mucopolysaccharides for a period of hours, the amount of BAP detected in the cartilage correlates to the proteoglycan and glycosaminoglycan content. Proteoglycan and glycosaminoglycan loss in hyaline cartilage is an early sign of osteoarthritis and therefore BAP and its pharmaceutically acceptable salts can be used as imaging agents for tracking cartilage health.

The terms used in these embodiments of the invention, such as labeled, imaging, cartilage, organ, smooth muscle fiber, tissue and additional therapeutic agent, have the same meaning as they have in the embodiments described in the preceding sections.

Figure 9:
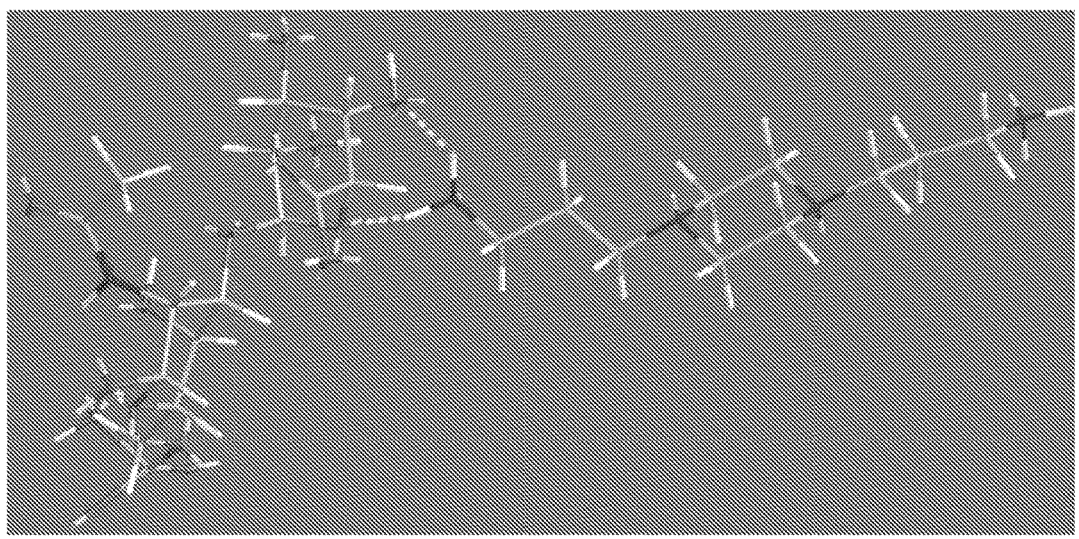
FIG. 9 is picture showing the results of an energy minimization molecular model that predicts the binding between 1,4-Bis(3-aminopropyl)piperazine ("BAP") and chondroitin sulfate.

FIG. 9 shows the results of an energy minimization model that predicts the binding between BAP and chondroitin sulfate, a major proteoglycan component of hyaline and elastic cartilage. Due to the non-covalent binding of BAP to the proteoglycan content of cartilage, the concentration of BAP in the cartilage should be directly related to its proteoglycan content. Reduced proteoglycan content in cartilage impairs the structural function of cartilage and can serve as a diagnostic for osteoarthritis and the likelihood of developing osteoarthritis amongst other conditions, disorders and diseases.

Another embodiment is a method of diagnosing a cartilage disorder or cartilage disease comprising: administering to a subject in need thereof a therapeutically effective amount of a pharmaceutical composition comprising a compound of formula IX, or a pharmaceutically acceptable salt thereof, and a pharmaceutically acceptable carrier, as described above; obtaining an image of the subject; and diagnosing a cartilage disorder or cartilage disease from the image.

In one embodiment, the pharmaceutical composition administered in a method of diagnosing a cartilage disorder or cartilage disease comprises the labeled compound of formula IX. Optionally, that pharmaceutical composition contains the labeled compound of formula IX and no unlabeled compound of that formula. In another embodiment, the pharmaceutical composition administered in a method of diagnosing a cartilage disorder or cartilage disease comprises the unlabeled compound of formula IX. Optionally, that pharmaceutical composition contains the unlabeled compound of formula IX and no labeled compound of that formula. In yet another embodiment, the pharmaceutical composition administered in a method of diagnosing a cartilage disorder or cartilage disease comprises both the labeled compound and the unlabeled compound of formula IX.

A further embodiment of the invention is directed to a method of monitoring cartilage health comprising administering to a subject in need thereof a therapeutically effective amount of a pharmaceutical composition comprising a compound of formula IX, or a pharmaceutically acceptable salt thereof, and a pharmaceutically acceptable carrier, as described above; obtaining an image of a cartilage in the subject; and quantifying the amount of the compound in the cartilage.

In one embodiment, the pharmaceutical composition administered in a method of monitoring cartilage health comprises the labeled compound of formula IX. Optionally, that pharmaceutical composition contains the labeled compound of formula IX and no unlabeled compound of that formula. In another embodiment, the pharmaceutical composition administered in a method of monitoring cartilage health comprises the unlabeled compound of formula IX. Optionally, that pharmaceutical composition contains the unlabeled compound of formula IX and no labeled compound of that formula. In yet another embodiment, the pharmaceutical composition administered in a method of monitoring cartilage health comprises both the labeled compound and the unlabeled compound of formula IX.

The entire contents of all references, patent applications, and patents cited throughout this application are hereby incorporated by reference herein.

EXAMPLES

The invention will be further illustrated in the following nonlimiting Examples. These Examples are set forth to aid in the understanding of the invention but are not intended to, and should not be construed to, limit its scope in any way. The Examples do not include detailed descriptions of conventional methods that are well known to those of ordinary skill in the art.

Example 1

In Vivo Testing of Labeled Di-Arginine Piperazine ("DAP")

A study was conducted to determine the pharmacokinetics, rates and routes of excretion with mass baseline and tissue distribution of radioactivity, after a single intravenous dose administration of formula XIII (also referred to as [$^{14}$C]DAP) was administered to the rats by tail vein intravenous injection at a dose of about 1.8 mg/kg. Formula XIII is depicted as follows and taught in commonly-owned U.S. Patent Provisional Application No. 61/901,646, the contents of which are incorporated by reference herein in their entirety:

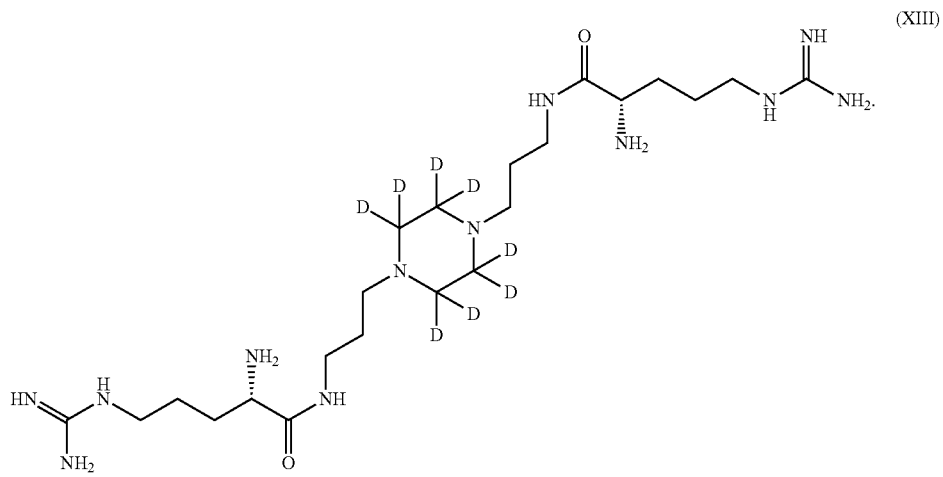 [SMILES: [2H]C1([2H])N(CCCNC(=O)[C@@H](N)CCCNC(=N)N)C([2H])([2H])C([2H])([2H])N(CCCNC(=O)[C@@H](N)CCCNC(=N)N)C1([2H])[2H]]

The study was conducted on 19 male rats divided into 4 groups. The first group of 6 rats was used for blood collection (Group 1); the second group of 4 rats was used for urine, feces, cage rinses and wipes and carcasses collection (Group 2); the third group of 4 rats was used for expired air collection (Group 3); the fourth group of 5 rats was used for terminal blood/serum and tissue distribution by Quantitative Whole-Body Autoradiography (QWBA) (Group 4).

For Group 4, formula XIII (QWBA was run at 1, 8, 12, 24 and 72 hours post dose. After terminal blood collection, each euthanized animal was frozen in a hexane/dry ice bath and embedded in a 2% carboxymethylcellulose matrix according to MPI Research SOP ADME-112. The embedded carcasses were sectioned according to MPI Research SOP ADME-113 on a Leica CM3600 Cyromacrotome set to maintain −10 to −30° C. At least four fortified quality control standards of known radioactive concentration were placed into the frozen block prior to sectioning and used for section thickness quality control. The quality control standards were sectioned under the same conditions as the specimen. The intrasection and intersection variation of collected sections were determined by analyzing the quality control standards. Section variation must be less than 20% for quantitative analysis. Sections that were approximately 40 μm thick were taken in the sagittal plane. Appropriate sections selected at various levels of interest in the block were collected to encompass the following tissues, organs, and biological fluids, where possible: adrenal gland, bladder (urinary) and contents (urine), blood (cardiac), bone, bone marrow, brain, eye, fat (brown), fat (white), heart, kidney, large intestine/cecum and contents, liver, lung, muscle, pancreas, prostate, salivary glands, skin, small intestine and contents, spleen, stomach and contents, testes, thymus, thyroid, mesenteric lymph nodes, and epididymis. A set of sections were mounted, exposed to phosphor imaging screens and scanned using the Storm 860 image acquisition system according to MPI Research SOP ADME-112. Quantification, relative to the calibration standards, were performed by image densitometry using MCID™ image analysis software according to MPI Research SOP ADME-114. A standard curve was constructed from the integrated response (MDC/mm2) and the nominal concentrations of the [$^{14}$C]Glucose calibration standards. Relative error should be less than 0.5 for each point on the curve. The concentrations of radioactivity were expressed as μCi/g and were converted to μg or ng-equivalents of DAP per gram of sample (μg- or ng-eq/g) using the specific activity of administered [$^{14}$C]DAP dose formulation. A lower limit of quantification (LLOQ) was applied to the data. The LLOQ was determined using the radioactive concentration of the lowest calibration standard used to generate a calibration curve divided by the specific activity of the dose formulation (μCi/ug). Artifacts, such as those produced by dislodged contents of the alimentary canal, were excluded from analysis during image analysis.

Results

FIGS. 1-5 are autoradiographs run at 1, 8, 12, 24 and 72 hours post dose on Group 4. It is clear from the 1 hour post dose autoradiograph (FIG. 1) that formula XIII and possibly its primary metabolites, labeled mono-arginine piperazine (MAP) and 1,4-bis(3-amino propyl) piperazine (BAP), distribute very well to cartilage and tissues. For example, the kidney, spleen, liver, pancreas, spinal cord, thymus, thyroid, lymph node, pituitary gland, harderian gland, olifactory lobe, medulla, myocardium, vitreous humor, and nasal turbinates are clearly identifiable in the autoradiograph, as well as abdominal fat, bone marrow, stomach and intestinal contents, urine and skin. In addition, both the articulating surfaces and the intervertebral discs in the thoracic vertebrae are clearly visible, as are the epiphyseal growth plates in the knee and shoulder joints.

After 8 hours (FIG. 2), the majority of [$^{14}$C]DAP (formula XIII) and any metabolites are no longer localized in all of the regions identifiable in FIG. 1. The compounds have already cleared from the body. With each increased interval of time after dosage, i.e., 12 hours, 24 hours and 72 hours, less cartilage and tissue is visible in the autoradiographs.

The concentration of radioactivity in blood and tissues of the rats from Group 4 over time following the single intravenous dose of [$^{14}$C]DAP is shown in Table 1 below. The shaded values indicate that, at one or more time points, the number of radioactive counts exceeded 3,000.

TABLE 1

Concentration of Radioactivity in Blood and Tissues of the Rats following a Single Intravenous Dose of [$^{14}$C] DAP (formula XIII) (2 mg/kg) Determined by QWBA

| | ng Equivalents [$^{14}$C]DAP/g Animal Number (Timepoint) | | | | |
|---|---|---|---|---|---|
| | 401 | 402 | 403 | 404 | 405 |
| | (1 | (8 | (12 | (24 | (72 |
| | Hour) | Hours) | Hours) | Hours) | Hours) |
| Tissue | A | B | C | D | E |
| Gastric mucosa | ND | ND | 2118 | 1438 | ND |
| Large intestinal contents | BLQ | 510 | 4752 | 1801 | 824 |
| Urine | 195176 | 8374 | 5011 | 4553 | 3866 |
| Cartilage | 62602 | 13038 | 7749 | ND | ND |
| Kidney (cortex) | 55358 | 45541 | 48959 | 40820 | 15748 |
| Kidney | 51966 | 43380 | 40930 | 39548 | 18515 |
| Urinary bladder | 26725 | 1429 | 1095 | 606 | 283 |
| Kidney (medulla) | 19308 | 3454 | 2981 | 2011 | 556 |
| Thymus | 10420 | 15093 | 14584 | 11451 | 8365 |
| Small intestine | 6838 | 6643 | 9975 | 5090 | 1597 |
| Bone marrow | 6820 | 5524 | 4948 | 1987 | 841 |
| Liver | 6377 | 3150 | 3330 | 2049 | 774 |
| Prostate gland | 4652 | 8806 | 9639 | 5272 | 4484 |
| Stomach | 4422 | 1348 | 1015 | 861 | 473 |
| Large intestine | 4060 | 2237 | 3594 | 2068 | 646 |
| Salivary gland | 4047 | 2060 | 2710 | 1447 | 487 |
| Lymph nodes | 3855 | 2192 | 2743 | 1348 | 550 |
| Pituitary gland | 3786 | 1802 | 2155 | 1463 | 638 |
| Preputial gland | 3702 | NR | 1611 | 927 | 639 |
| Spleen | 3699 | 1896 | 1793 | 1007 | 408 |
| Exorbital gland | 3586 | 1415 | 1733 | 931 | 304 |
| Lung | 3486 | 1635 | 1534 | 1087 | 545 |
| Intraorbital gland | 3349 | 1660 | 1632 | 1059 | 298 |
| Nasal turbinates | 3326 | 3117 | 3378 | 2635 | 1204 |
| Skin | 3318 | 1893 | 1982 | 1073 | 375 |
| Small intestinal contents | 3191 | 1019 | 1305 | 462 | 320 |
| Cecum | 3182 | 1868 | 2648 | 1256 | ND |
| Pancreas | 2923 | 2819 | 3058 | 1702 | 360 |
| Bulbourethral gland | 2841 | 1086 | 3753 | 535 | ND |
| Thyroid gland | 2805 | 2049 | 2667 | 1641 | 510 |
| Fat (brown) | 2750 | 1097 | 1689 | 1441 | 593 |
| Uveal tract | 2565 | ND | ND | ND | ND |
| Epididymis | 2539 | 1041 | 592 | 722 | BLQ |
| Esophagus | 2248 | 1842 | 1288 | 822 | ND |
| Myocardium | 1978 | 832 | 912 | 538 | 264 |
| Blood | 1794 | 328 | 212 | 209 | BLQ |
| Diaphragm | 1782 | 582 | 603 | 448 | 206 |
| Adrenal gland | 1747 | 715 | 755 | 564 | 341 |
| Harderian gland | 1506 | 846 | 1004 | 897 | 458 |
| Fat (white) | 1144 | 485 | 494 | 527 | 236 |
| Testes | 895 | 444 | 415 | 330 | BLQ |
| Muscle | 717 | 405 | 341 | 279 | BLQ |
| Olfactory lobe | 609 | 386 | 435 | 614 | 213 |
| Cecum contents | 543 | 1134 | 2391 | 814 | 421 |
| Esophageal contents | 498 | 434 | 185 | 196 | ND |
| Vitreous humor | 494 | 322 | 261 | 309 | ND |
| Bone | 445 | 250 | 356 | 506 | BLQ |
| Seminal vesicles | 331 | 274 | 283 | 183 | BLQ |
| Eye (lens) | 325 | 183 | 176 | BLQ | ND |
| Cerebrum | 252 | 228 | BLQ | 397 | 182 |
| Cerebellum | 223 | 180 | BLQ | 298 | BLQ |
| Spinal cord | 213 | 187 | BLQ | BLQ | BLQ |
| Stomach contents | 196 | 368 | BLQ | BLQ | BLQ |
| Medulla | 188 | 204 | BLQ | 200 | BLQ |

TABLE 1-continued

Concentration of Radioactivity in Blood and Tissues of the Rats following a Single Intravenous Dose of [$^{14}$C] DAP (formula XIII) (2 mg/kg) Determined by QWBA

| | ng Equivalents [$^{14}$C]DAP/g Animal Number (Timepoint) | | | | |
|---|---|---|---|---|---|
| | 401 | 402 | 403 | 404 | 405 |
| | (1 | (8 | (12 | (24 | (72 |
| | Hour) | Hours) | Hours) | Hours) | Hours) |
| Tissue | A | B | C | D | E |

BLQ = Below limit of quantitation (<172 ng equivalents [$^{14}$C]PER977/g).
ND = Not detectable (sample shape not discernible from background or surrounding tissue).
NR = Not represented (tissue not represented on section).

Figure 6:
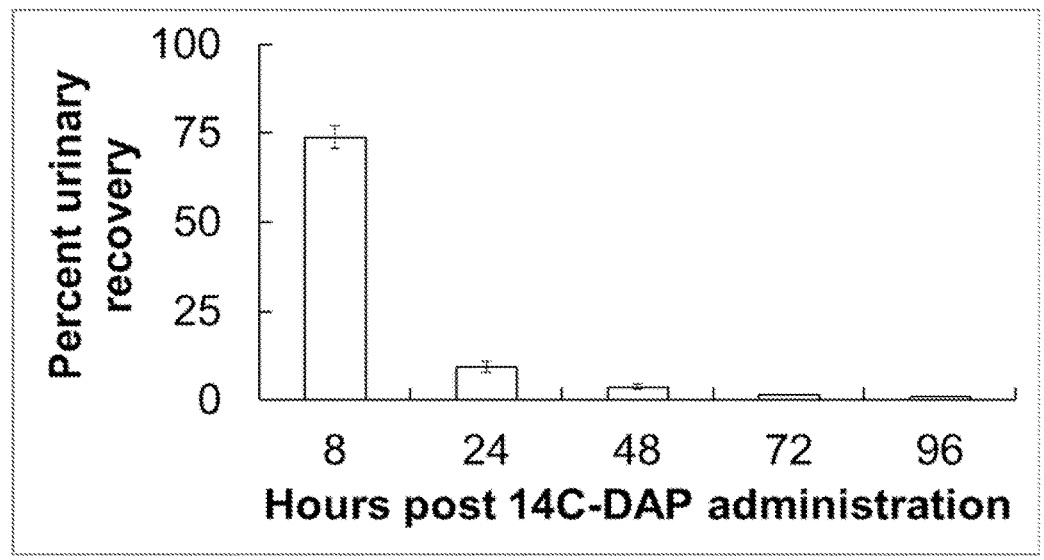
FIG. 6 shows urinary excretion kinetics of percent urinary recovery over time after a single intravenous dose of formula XIII (also referred to as [$^{14}$C]DAP) was administered to a rat by tail vein intravenous injection at a dose of about 1.8 mg/kg.

The short residence time and rapid clearing of formula XIII from the body may also be measured by reviewing urinary excretion kinetics. FIG. 6 is a graph of percent urinary recovery over time after administration. As shown in this graph, the vast majority of labeled DAP is excreted well in advance of 24 hours after administration.

Figure 7:
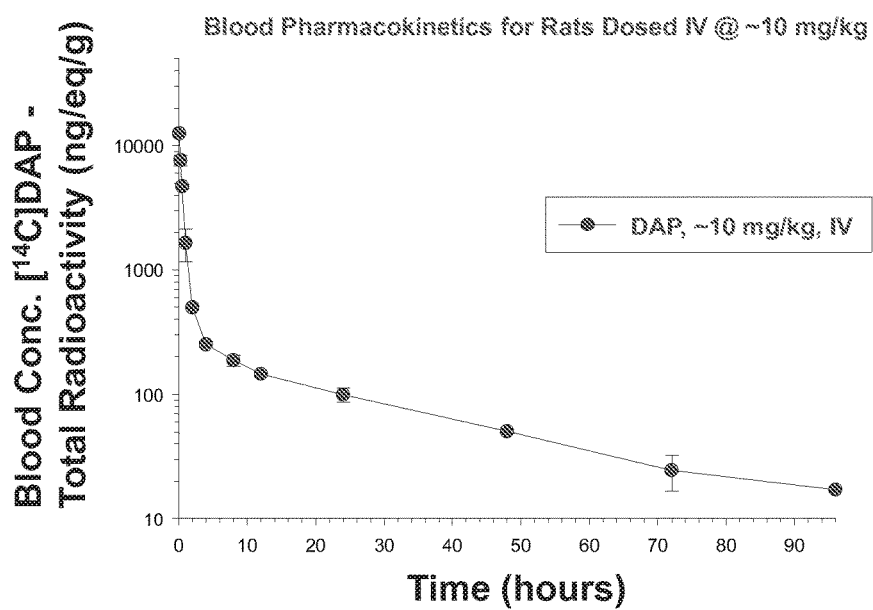
FIG. 7 illustrates graph of [$^{14}$C]DAP and BAP Mass Balance PK Results in blood concentration (ng-eq/g) over time.
Figure 8:
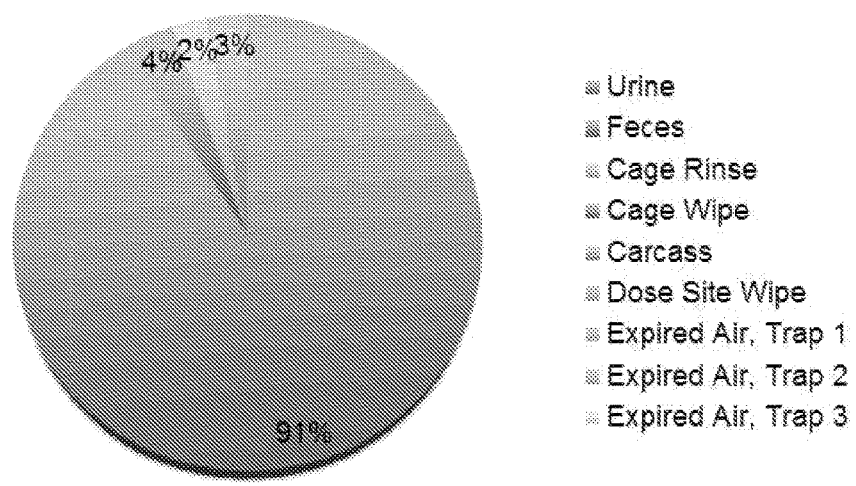
FIG. 8 is a graph of [$^{14}$C]DAP recovery.

The results of the samples collected from Groups 2 and 3 are shown in FIGS. 7 and 8. FIG. 7 is a graph showing blood concentration and total radioactivity in ng-eq/g. These data show the pharmacokinetic and excretion profiles of intravenously administered labeled DAP. FIG. 8 is a graph showing total recovery of formula XIII is 98.21±0.4% and also presents data representing how the compound was cleared from the body. The raw data for the rat mass balance recovery after the single intravenous administration to Groups 2 and 3 is shown in Table 2 below.

TABLE 2

Rat Mass Balance Recovery following Intravenous Dose of Formula XIII in Groups 2 and 3

| Sample | Timepoint (hrs) | 201M | 202M | 203M | 204M | Mean | SD |
|---|---|---|---|---|---|---|---|
| Urine | 0-8 | 71.47 | 75.10 | 71.13 | 77.45 | 73.79 | 3.03 |
| Urine | 8-24 | 11.56 | 9.15 | 9.65 | 7.62 | 9.50 | 1.63 |
| Urine | 24-48 | 3.83 | 3.59 | 4.50 | 2.92 | 3.71 | 0.65 |
| Urine | 48-72 | 1.61 | 1.73 | 1.61 | 1.36 | 1.58 | 0.16 |
| Urine | 72-96 | 0.97 | 1.03 | 0.96 | 0.79 | 0.94 | 0.10 |
| Subtotal | | 89.44 | 90.60 | 87.85 | 90.14 | 89.51 | 1.20 |
| Feces | 0-8 | 0.00 | 0.04 | 0.01 | 0.04 | 0.02 | 0.02 |
| Feces | 8-24 | 1.34 | 2.04 | 2.40 | 1.49 | 1.82 | 0.49 |
| Feces | 24-48 | 1.18 | 0.70 | 1.15 | 0.70 | 0.93 | 0.27 |
| Feces | 48-72 | 0.46 | 0.41 | 0.54 | 0.26 | 0.42 | 0.12 |
| Feces | 72-96 | 0.31 | 0.26 | 0.27 | 0.15 | 0.25 | 0.07 |
| Subtotal | | 3.29 | 3.45 | 4.37 | 2.64 | 3.44 | 0.71 |
| Cage Rinse | 0-24 | 2.48 | 0.91 | 1.94 | 1.63 | 1.74 | 0.66 |
| Cage Rinse | 24-48 | 0.37 | 0.21 | 0.38 | 0.30 | 0.32 | 0.08 |
| Cage Rinse | 48-72 | 0.13 | 0.11 | 0.20 | 0.28 | 0.18 | 0.08 |
| Cage Rinse | 72-96 | 0.12 | 0.11 | 0.24 | 0.15 | 0.16 | 0.06 |
| Subtotal | | 3.10 | 1.34 | 2.76 | 2.36 | 2.39 | 0.76 |
| Cage Wipe | 96 | 0.08 | 0.06 | 0.20 | 0.04 | 0.10 | 0.07 |
| Carcass | 96 | 2.74 | 2.80 | 2.60 | 2.68 | 2.71 | 0.09 |
| Dose Site Wipe | 0 | 0.01 | 0.01 | 0.00 | 0.01 | 0.01 | 0.01 |

| | | 301M | 302M | 303M | 304M | | |
|---|---|---|---|---|---|---|---|
| Expired Air, Trap 1 | 0-24 | 0.03 | 0.03 | 0.02 | 0.03 | 0.03 | 0.01 |
| Expired Air, Trap 1 | 24-48 | 0.00 | 0.00 | 0.00 | 0.00 | 0.00 | 0.00 |

TABLE 2-continued

Rat Mass Balance Recovery following Intravenous Dose of Formula XIII in Groups 2 and 3

| | | | | | | | |
|---|---|---|---|---|---|---|---|
| Expired Air, Trap 1 | 48-72 | 0.00 | 0.00 | 0.00 | 0.05 | 0.01 | 0.03 |
| | Subtotal | 0.03 | 0.03 | 0.02 | 0.08 | 0.04 | 0.03 |
| Expired Air, Trap 2 | 0-24 | 0.02 | 0.02 | 0.02 | 0.02 | 0.02 | 0.00 |
| Expired Air, Trap 2 | 24-48 | 0.00 | 0.00 | 0.00 | 0.00 | 0.00 | 0.00 |
| Expired Air, Trap 2 | 48-72 | 0.00 | 0.00 | 0.00 | 0.00 | 0.00 | 0.00 |
| | Subtotal | 0.02 | 0.02 | 0.02 | 0.02 | 0.02 | 0.00 |
| Expired Air, Trap 3 | 0-24 | 0.01 | 0.01 | 0.01 | 0.01 | 0.01 | 0.00 |
| Expired Air, Trap 3 | 24-48 | 0.00 | 0.00 | 0.00 | 0.00 | 0.00 | 0.00 |
| Expired Air, Trap 3 | 48-72 | 0.00 | 0.00 | 0.00 | 0.00 | 0.00 | 0.00 |
| | Subtotal | 0.01 | 0.01 | 0.01 | 0.01 | 0.01 | 0.00 |
| | TOTAL | 98.72 | 98.32 | 97.83 | 97.98 | 98.21 | 0.40 |

201M through 204M identify each of the four rats in Group 2 and 301M through 304M identify each of the four rats in Group 3.

The blood drawn from Group 1 was tested for PK values and presented in Table 3. Blood PK and blood to serum ratios for Group 4 are depicted in Table 4.

TABLE 3

Rat Blood PK Samples after Intravenous Injection of Group 1

| Timepoint (hrs) | 101M | 102M | 103M | 104M | 105M | 106M | Mean | SD |
|---|---|---|---|---|---|---|---|---|
| 0.083 | 12283.00 | 12343.00 | 12856.00 | | | | 12494.00 | 314.93 |
| 0.250 | | | | 6989.90 | 8433.50 | 7487.20 | 7636.87 | 733.35 |
| 0.5 | 4890.10 | 4595.70 | 4661.50 | | | | 4715.77 | 154.52 |
| 1 | | | | 1277.80 | 2173.10 | 1466.70 | 1639.20 | 471.92 |
| 2 | 513.73 | 503.14 | 474.26 | | | | 497.04 | 20.43 |
| 4 | | | | 244.30 | 269.75 | 239.03 | 251.03 | 16.43 |
| 8 | 207.32 | 187.12 | 169.19 | | | | 187.88 | 19.08 |
| 12 | | | | 149.71 | 148.64 | 138.94 | 145.76 | 5.93 |
| 24 | 105.64 | 108.29 | 84.43 | | | | 99.45 | 13.08 |
| 48 | | | | 49.28 | 52.03 | 50.38 | 50.56 | 1.38 |
| 72 | 23.54 | 33.09 | 17.27 | | | | 24.63 | 7.97 |
| 96 | | | | 17.39 | 16.69 | 17.60 | 17.23 | 0.48 |

TABLE 4

Rat Blood PK and Blood to Serum Ratio of Group 4

| Sample | Timepoint (hrs) | 401M | 402M | 403M | 404M | 405M |
|---|---|---|---|---|---|---|
| Blood | 1 | 1602.10 | | | | |
| Blood | 8 | | 147.98 | | | |
| Blood | 12 | | | 135.75 | | |
| Blood | 24 | | | | 125.15 | |
| Blood | 72 | | | | | 29.93 |
| Serum | 1 | 3605.20 | | | | |
| Serum | 8 | | 111.94 | | | |
| Serum | 12 | | | 73.59 | | |
| Serum | 24 | | | | 55.21 | |
| Serum | 72 | | | | | 11.84 |
| Blood:Serum Ratio | 1 | 0.44 | | | | |
| Blood:Serum Ratio | 8 | | 1.32 | | | |
| Blood:Serum Ratio | 12 | | | 1.84 | | |
| Blood:Serum Ratio | 24 | | | | 2.27 | |
| Blood:Serum Ratio | 72 | | | | | 2.53 |

In this study, because the compound of formula XIII is [$^{14}$C]-labeled, autoradiography was used for detection. When using non-labeled DAP in accordance with the present invention, one would anticipate the same or very similar distribution to cartilage and tissues, localization, residence time and other results, since the substitution of [$^{14}$C] for [$^{12}$C] should not affect tissue distribution. However, when using the non-labeled compounds disclosed herein, imaging would be better performed using chemical shift imaging.

Example 2

In Vivo Toxicity Studies of Labeled DAP

A study was conducted to test the toxicity of labeled formula XIII in rats and dogs. Maximum tolerated doses were 40 mg/kg for rats and 35 mg/kg for dogs.

Example 3

In Vivo Safety Studies of Labeled DAP

A study was conducted to test the safety profile of labeled formula XIII in humans in intravenous bolus doses up to 200 mg. These doses were administered with an excellent safety profile.

What is claimed is:
1. A method of imaging comprising:
    administering to a subject in need thereof, as an imaging agent, a therapeutically effective amount of a compound selected from the group consisting of formulae (IX)-(XII) or a pharmaceutically acceptable salt thereof:

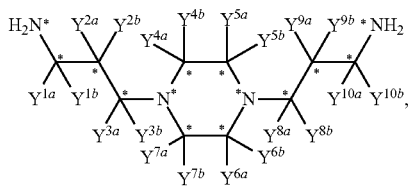
(IX)

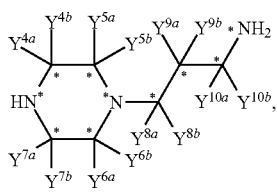
(X)

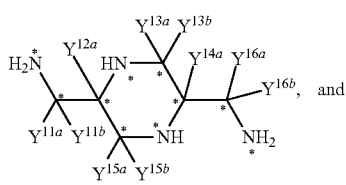
(XI)

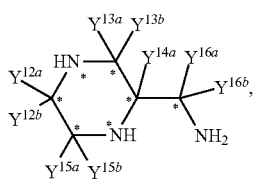
(XII)

wherein:
  each Y is independently selected from hydrogen, deuterium, or tritium;
  each carbon denoted with an asterisk is independently selected from $^{12}C$, $^{13}C$, and $^{14}C$; and
  each nitrogen denoted with an asterisk is independently selected from $^{14}N$ and $^{15}N$; and
obtaining an image.

2. The method of claim 1, wherein the compound or the pharmaceutically acceptable salt thereof is labeled.

3. The method of claim 1, wherein the compound or the pharmaceutically acceptable salt thereof is unlabeled.

4. The method of claim 2, wherein the compound of formula (IX) is administered.

5. The method of claim 2, wherein the compound of formula (IX) or the pharmaceutically acceptable salt thereof is administered.

6. The method of claim 3, wherein the compound of formula (IX) is administered.

7. The method of claim 3, wherein the compound of formula (IX) or the pharmaceutically acceptable salt thereof is administered.

8. The method of claim 1, wherein the image is obtained using magnetic resonance imaging.

9. The method of claim 8, wherein the magnetic resonance imaging is chemical shift imaging.

10. The method of claim 1, wherein the image is obtained using radiography.

11. The method of claim 1, wherein the method further comprises assessing osteoarthritis by tracking proteoglycan and glycosaminoglycan content of cartilage in the image.

12. The method of claim 1, wherein the method further comprises diagnosing a growth disorder from the image.

13. The method of claim 1, wherein the image is a urogram.

14. The method of claim 1, wherein the method further comprises detecting an inflamed cartilage or an inflamed joint in the image.

15. The method of claim 1, wherein the compound localizes in a cartilage, an organ, a smooth muscle fiber, and/or a tissue.

16. The method of claim 15, wherein the compound localizes in the cartilage and is present in a concentration of about 10 micromolar to about 100 millimolar.

17. The method of claim 1, wherein the subject is a mammal.

18. The method of claim 1, wherein the compound resides in a cartilage, an organ, a smooth muscle fiber, and/or a tissue for about 1 hour to about 24 hours.

19. The method of claim 1, wherein the therapeutically effective amount is about 0.001 mg/kg to about 1 g/kg of body weight per day, and
  wherein the compound is administered intravenously, intra-articularly or orally.

20. A labeled compound of formula (IX) or a pharmaceutically acceptable salt thereof:

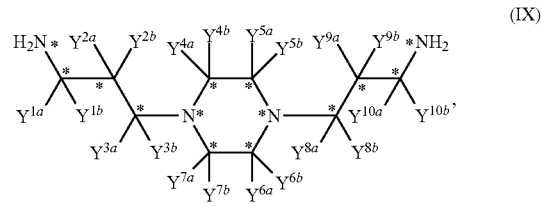
(IX)

wherein:
  each Y is independently selected from hydrogen, deuterium, or tritium;
  each carbon denoted with an asterisk is independently selected from $^{12}C$, $^{13}C$, and $^{14}C$; and
  each nitrogen denoted with an asterisk is independently selected from $^{14}N$ and $^{15}N$, and
  wherein the compound includes at least one of $^{13}C$, $^{14}C$, $^{15}N$, deuterium, and tritium.

21. The method of claim 4, wherein the image is obtained using magnetic resonance imaging, and
  wherein the image includes an image of a cartilage.

22. The method of claim 6, wherein the image is obtained using magnetic resonance imaging, and
  wherein the image includes an image of a cartilage.

23. A method of imaging comprising:
  providing to a cartilage, an organ, a smooth muscle fiber, and/or a tissue of a subject, as an imaging agent, a compound selected from the group consisting of formulae (IX)-(XII) or a pharmaceutically acceptable salt thereof:

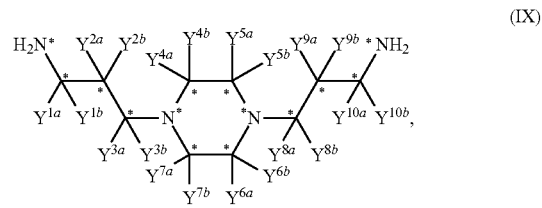
(IX)

-continued

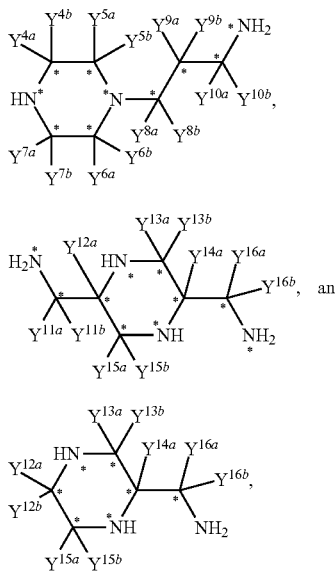

wherein:
each Y is independently selected from hydrogen, deuterium, or tritium;
each carbon denoted with an asterisk is independently selected from $^{12}C$, $^{13}C$, and $^{14}C$; and
each nitrogen denoted with an asterisk is independently selected from $^{14}N$ and $^{15}N$; and
obtaining an image of the cartilage, the organ, the smooth muscle fiber, and/or the tissue.

24. The method of claim 23, wherein the compound or the pharmaceutically acceptable salt thereof is labeled.

25. The method of claim 23, wherein the compound or the pharmaceutically acceptable salt thereof is unlabeled.

26. The method of claim 24, wherein the imaging agent is the compound of formula (IX).

27. The method of claim 26, wherein the image is obtained using magnetic resonance imaging.

28. The method of claim 27, wherein the image of the cartilage is obtained.

29. The method of claim 25, wherein the imaging agent is the compound of formula (IX).

30. The method of claim 29, wherein the image is obtained using magnetic resonance imaging.

31. The method of claim 30, wherein the image of the cartilage is obtained.

32. The method of claim 24, wherein the imaging agent is the compound of formula (IX) or the pharmaceutically acceptable salt thereof.

33. The method of claim 25, wherein the imaging agent is the compound of formula (IX) or the pharmaceutically acceptable salt thereof.

34. The method of claim 1, wherein the subject is a human.

35. The method of claim 23, wherein the subject is a human.

36. The method of claim 26, wherein the subject is a human.

37. The method of claim 29, wherein the subject is a human.

38. The compound of claim 20, comprising at least one of $^{13}C$, $^{14}C$, and $^{15}N$.

* * * * *